(12) United States Patent
Lee et al.

(10) Patent No.: US 10,076,290 B2
(45) Date of Patent: Sep. 18, 2018

(54) X-RAY IMAGING APPARATUS AND CONTROL METHOD FOR THE SAME

(71) Applicant: Samsung Electronics Co., Ltd, Gyeonggi-do (KR)

(72) Inventors: Seung Hwan Lee, Seoul (KR); Sang Kyun Kang, Gyeonggi-do (KR); Se Hui Kim, Gyeonggi-do (KR); Ku-Il Jang, Gyeonggi-do (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 15/260,245

(22) Filed: Sep. 8, 2016

(65) Prior Publication Data

US 2017/0065246 A1   Mar. 9, 2017

(30) Foreign Application Priority Data

Sep. 8, 2015   (KR) .......................... 10-2015-0126782

(51) Int. Cl.
*A61B 6/00*   (2006.01)
*A61B 6/08*   (2006.01)
*A61B 6/06*   (2006.01)

(52) U.S. Cl.
CPC .................. *A61B 6/08* (2013.01); *A61B 6/06* (2013.01); *A61B 6/4405* (2013.01); *A61B 6/547* (2013.01); *A61B 6/588* (2013.01); *A61B 6/467* (2013.01)

(58) Field of Classification Search
CPC ........... A61B 6/08; A61B 6/547; A61B 6/467; A61B 6/588

(Continued)

(56) References Cited

U.S. PATENT DOCUMENTS 3,629,594 A * 12/1971 Sandberg ................. A61B 6/08
                                                    250/221
4,060,733 A * 11/1977 Franke ..................... A61B 6/08
                                                    378/206

(Continued)

FOREIGN PATENT DOCUMENTS

WO   WO2014173741 A1   10/2014

OTHER PUBLICATIONS

Foreign Communication From a Related Counterpart Application, PCT Application No. PCT/KR2016/010029, International Search Report dated Dec. 28, 2016, 3 pages.

(Continued)

*Primary Examiner* — Allen C. Ho

(57) ABSTRACT

An X-ray imaging apparatus and control method for the same relate to a mobile X-ray imaging apparatus that allows a user to recognize whether the X-ray imaging apparatus is in an appropriate imaging distance from an object. The X-ray imaging apparatus includes an X-ray source, an input unit that receives distance information between the X-ray source and an X-ray detector, a reference light emitter that irradiates a light from the X-ray source in a direction where the X-ray detector is placed, at least one auxiliary light emitter that irradiates a light that overlaps with a light from the reference light emitter; and a controller that determines an auxiliary light emitter corresponding to the distance information among the at least one auxiliary light emitter, and controls the reference light emitter and the determined auxiliary light emitter so that the reference light emitter and the determined auxiliary light emitter irradiate a light.

17 Claims, 26 Drawing Sheets

(58) Field of Classification Search
USPC .................................................. 378/205, 206
See application file for complete search history.

(56) References Cited

U.S. PATENT DOCUMENTS

| | | | | |
|---|---|---|---|---|
| 4,092,544 A * | 5/1978 | Grim | ............... | A61B 6/587 378/114 |
| 4,167,675 A * | 9/1979 | Stödberg | ............... | A61B 6/08 378/153 |
| 4,246,486 A * | 1/1981 | Madsen | ............... | A61B 6/587 378/206 |
| 4,293,771 A * | 10/1981 | Lescrenier | ............... | A61B 6/08 356/138 |
| 4,356,400 A * | 10/1982 | Polizzi | ............... | A61B 6/587 250/252.1 |
| 4,426,726 A * | 1/1984 | Cheetham | ............... | A61B 90/13 378/206 |
| 4,618,980 A * | 10/1986 | Lescrenier | ............... | G21K 1/04 378/205 |
| 4,670,896 A * | 6/1987 | Klausz | ............... | A61B 6/00 378/156 |
| 4,836,671 A * | 6/1989 | Bautista | ............... | A61B 6/587 250/491.1 |
| 4,896,343 A * | 1/1990 | Saunders | ............... | A61B 6/08 378/206 |
| 5,136,627 A * | 8/1992 | Conrads | ............... | A61B 6/08 378/146 |
| 5,212,720 A * | 5/1993 | Landi | ............... | A61B 6/08 33/262 |
| 5,241,578 A * | 8/1993 | MacMahon | ............... | A61B 6/587 378/154 |
| 5,316,014 A * | 5/1994 | Livingston | ............... | A61B 17/3403 378/206 |
| 5,517,546 A * | 5/1996 | Schmidt | ............... | A61B 6/08 378/205 |
| 5,553,115 A * | 9/1996 | Odaka | ............... | A61B 6/08 378/170 |
| 5,572,568 A * | 11/1996 | Kanemitsu | ............... | A61B 6/08 378/190 |
| 5,598,269 A * | 1/1997 | Kitaevich | ............... | A61B 6/08 356/399 |
| 5,657,368 A * | 8/1997 | Röckseisen | ............... | A61B 6/08 378/206 |
| 5,707,360 A * | 1/1998 | Röckseisen | ............... | A61B 17/3403 378/206 |
| 5,844,962 A * | 12/1998 | Kunert | ............... | G21K 1/04 378/150 |
| 6,036,362 A * | 3/2000 | Schmitt | ............... | A61B 6/08 378/150 |
| 6,041,249 A * | 3/2000 | Regn | ............... | A61B 6/08 378/20 |
| 6,044,291 A * | 3/2000 | Röckseisen | ............... | A61B 6/08 378/206 |
| 6,048,097 A * | 4/2000 | Heinze | ............... | A61B 6/08 378/205 |
| 6,187,018 B1 * | 2/2001 | Sanjay-Gopal | ............... | A61B 90/36 600/426 |
| 6,267,502 B1 * | 7/2001 | McNeirney | ............... | A61B 6/08 378/205 |
| 6,305,842 B1 * | 10/2001 | Kunert | ............... | A61B 6/08 378/147 |
| 6,435,717 B1 * | 8/2002 | Köhler | ............... | A61B 6/107 378/205 |
| 6,447,164 B1 * | 9/2002 | Polkus | ............... | A61B 6/08 378/205 |
| 6,478,462 B2 * | 11/2002 | Polkus | ............... | A61B 6/4233 378/205 |
| 6,502,984 B2 * | 1/2003 | Ogura | ............... | A61B 6/06 378/206 |
| 6,522,908 B1 * | 2/2003 | Miyashita | ............... | A61B 5/0064 600/409 |
| 6,814,489 B2 * | 11/2004 | Jensen | ............... | A61B 6/08 378/197 |
| 6,821,017 B1 * | 11/2004 | Tankersley | ............... | A61B 6/4429 378/205 |
| 7,014,362 B2 * | 3/2006 | Beimier | ............... | A61B 6/08 378/162 |
| 7,040,807 B2 * | 5/2006 | Scheuering | ............... | A61B 6/08 356/399 |
| 7,050,544 B2 * | 5/2006 | Karlsson | ............... | A61B 6/502 378/148 |
| 7,104,689 B2 * | 9/2006 | Ihalainen | ............... | A61B 6/08 378/206 |
| 7,108,423 B2 * | 9/2006 | Schmitt | ............... | A61B 6/08 378/147 |
| 7,114,849 B2 * | 10/2006 | Atzinger | ............... | A61B 6/08 378/206 |
| 7,147,370 B2 * | 12/2006 | Xu | ............... | A61B 6/08 378/205 |
| 7,147,371 B2 * | 12/2006 | Hecker | ............... | A61B 6/08 378/204 |
| 7,290,930 B2 * | 11/2007 | Hoheisel | ............... | A61B 6/08 378/205 |
| 7,344,305 B2 * | 3/2008 | Kuzmanovic | ............... | A61B 6/08 378/205 |
| 7,380,986 B2 * | 6/2008 | Brandstätter | ............... | A61B 6/08 378/206 |
| 7,382,866 B2 * | 6/2008 | Tan | ............... | A61B 6/06 378/147 |
| 7,413,344 B2 * | 8/2008 | Qian | ............... | G01N 23/04 378/147 |
| 7,490,986 B2 * | 2/2009 | Takekoshi | ............... | A61B 6/4441 378/205 |
| 7,543,988 B2 * | 6/2009 | Ramsauer | ............... | A61B 6/0414 378/206 |
| 7,545,914 B2 * | 6/2009 | Kito | ............... | A61B 6/4283 378/207 |
| 7,559,693 B2 * | 7/2009 | Sonani | ............... | A61B 6/08 378/206 |
| 7,581,884 B1 * | 9/2009 | Barnes | ............... | A61B 6/06 378/164 |
| 7,632,015 B2 * | 12/2009 | Stayman | ............... | A61B 6/032 378/163 |
| 7,677,801 B2 * | 3/2010 | Pakzaban | ............... | A61B 5/103 378/162 |
| 7,697,147 B2 * | 4/2010 | Kindlein | ............... | A61B 6/08 356/601 |
| 7,736,055 B2 * | 6/2010 | Hörnig | ............... | A61B 6/08 378/206 |
| 7,737,427 B2 * | 6/2010 | Kito | ............... | A61B 6/4233 250/370.08 |
| 7,742,569 B2 * | 6/2010 | Graumann | ............... | A61B 6/00 378/206 |
| 7,794,144 B2 * | 9/2010 | Windt | ............... | A61B 6/08 378/206 |
| 7,798,709 B2 * | 9/2010 | Haras | ............... | A61B 6/032 378/206 |
| 7,802,919 B2 * | 9/2010 | Hessert | ............... | B23Q 17/2233 378/206 |
| 7,806,591 B2 * | 10/2010 | Wang | ............... | A61B 6/00 378/196 |
| 7,878,710 B2 * | 2/2011 | Kashiwagi | ............... | A61B 6/502 378/206 |
| 8,064,572 B2 * | 11/2011 | Sato | ............... | A61B 6/4429 378/206 |
| 8,149,987 B2 * | 4/2012 | Ogura | ............... | A61B 6/025 378/115 |
| 8,155,269 B2 * | 4/2012 | Kobayashi | ............... | A61B 6/08 378/164 |
| 8,165,660 B2 * | 4/2012 | Pfister | ............... | A61B 6/12 378/206 |
| 8,317,394 B2 * | 11/2012 | Klemm | ............... | A61B 6/08 378/108 |
| 8,371,751 B2 * | 2/2013 | Vazquez | ............... | A61B 5/1128 378/206 |
| 8,434,942 B2 * | 5/2013 | Lenchig, Jr. | ............... | A61B 6/08 378/204 |
| 8,467,495 B2 * | 6/2013 | Okada | ............... | A61B 6/022 378/206 |

(56) References Cited

U.S. PATENT DOCUMENTS

| | | | | |
|---|---|---|---|---|
| 8,767,913 B2* | 7/2014 | Okuno | ............... | A61B 6/08 378/206 |
| 8,798,230 B2* | 8/2014 | Cho | ............... | A61B 6/405 378/15 |
| 8,821,015 B2* | 9/2014 | Stagnitto | ............... | A61B 6/4291 378/205 |
| 8,821,017 B2* | 9/2014 | Lalena | ............... | A61B 6/08 378/206 |
| 8,827,554 B2* | 9/2014 | Lalena | ............... | A61B 6/46 378/206 |
| 8,861,679 B2* | 10/2014 | Suuronen | ............... | A61B 6/00 378/98.5 |
| 9,028,145 B2* | 5/2015 | Laws | ............... | A61B 6/08 378/145 |
| 9,039,283 B2* | 5/2015 | Graumann | ............... | A61B 6/08 378/205 |
| 9,049,996 B2* | 6/2015 | Tsujii | ............... | A61B 6/022 |
| 9,050,023 B2* | 6/2015 | Okuno | ............... | A61B 6/08 |
| 9,149,654 B2* | 10/2015 | Handa | ............... | A61N 5/1049 |
| 9,232,923 B2* | 1/2016 | Lee | ............... | A61B 6/022 |
| 9,265,467 B2* | 2/2016 | Kamiya | ............... | A61B 6/5241 |
| 9,433,395 B2* | 9/2016 | Kang | ............... | A61B 6/544 |
| 9,439,619 B1* | 9/2016 | Nance | ............... | A61B 6/587 |
| 9,521,983 B2* | 12/2016 | Jang | ............... | A61B 6/4429 |
| 9,521,987 B2* | 12/2016 | Tajima | ............... | A61B 6/08 |
| 9,579,071 B2* | 2/2017 | Lee | ............... | A61B 6/022 |
| 9,649,084 B2* | 5/2017 | Kim | ............... | A61B 6/544 |
| 9,675,309 B2* | 6/2017 | Kim | ............... | A61B 6/4266 |
| 9,730,669 B2* | 8/2017 | Lee | ............... | A61B 6/545 |
| 9,820,705 B2* | 11/2017 | Kim | ............... | A61B 6/08 |
| 9,861,327 B2* | 1/2018 | Yasuda | ............... | A61B 6/08 |
| 2003/0185349 A1* | 10/2003 | Roeckseisen | ............... | A61B 6/08 378/206 |
| 2004/0141590 A1 | 7/2004 | Ihalainen | | |
| 2006/0126796 A1 | 6/2006 | Hecker | | |
| 2009/0041201 A1 | 2/2009 | Wang et al. | | |
| 2011/0249793 A1 | 10/2011 | Lalena et al. | | |
| 2013/0142304 A1 | 6/2013 | Shiraishi et al. | | |
| 2014/0341349 A1 | 11/2014 | Lalena et al. | | |

OTHER PUBLICATIONS

Foreign Communication from Related Counterpart Application; Korean Patent Application No. 10-2015-0126782; Notice of Allowance dated Aug. 14, 2017; 7 pages.

Foreign Communication from Related Counterpart Application; European Patent Application No. 16813344.5; Extended European Search Report and European Search Opinion dated Aug. 8, 2017; 5 pages.

* cited by examiner

X-RAY IMAGING APPARATUS AND CONTROL METHOD FOR THE SAME

CROSS-REFERENCE TO RELATED APPLICATION(S) AND CLAIM OF PRIORITY

The present application is related to and claims the benefit of Korean Patent Application No. 10-2015-0126782, filed on Sep. 8, 2015 in the Korean Intellectual Property Office, the disclosure of which is incorporated herein by reference.

TECHNICAL FIELD

Embodiments of the present disclosure relate to a mobile X-ray imaging apparatus configured to generate an X-ray image by transmitting X-rays to an object, and a control method of the same.

BACKGROUND

An X-ray imaging apparatus noninvasively acquires images of the inner structure of an object by emitting X-rays to the object and detecting the penetrated X-rays. Since transmittance of X-rays vary according to a structure forming an object, the inner structure of an object may be imaged by using attenuation coefficient that is digitalized a difference of the transmittance.

Because an X-ray imaging apparatus in a conventional manner, includes an X-ray source and an X-ray detector that may be fixed to a certain space, a patient should move to an examination room in which the X-ray imaging apparatus is placed, and the patient may be needed to move his/her body to fit the X-ray imaging apparatus.

However, there may be a difficulty in scanning a patient having difficulty moving with a conventional X-ray imaging apparatus, and thus a mobile X-ray imaging apparatus has been developed to perform an X-ray imaging regardless of places.

The mobile X-ray imaging apparatus may come to a patient having difficulty moving so as to perform an X-ray imaging thanks to an X-ray source being mounted to a mobile body, and a portable X-ray detector.

When performing an X-ray imaging on an object by using an X-ray imaging apparatus, a source-image distance (SID) may be determined according to the type of X-ray imaging and a target part of the object.

SUMMARY

To address the above-discussed deficiencies, it is a primary object to provide an X-ray imaging apparatus and a control method of the same, particularly a mobile X-ray imaging apparatus capable of allowing a user to intuitively recognize whether the X-ray imaging apparatus is placed in an appropriate imaging distance from an object, by an overlap of a light wherein the light is irradiated from a plurality of light emitters that is set according to pre-stored source image distance (SID) information.

Additional aspects of the present disclosure will be set forth in part in the description which follows and, in part, will be obvious from the description, or may be learned by practice of the disclosure.

In accordance with one aspect of the present disclosure, an X-ray imaging apparatus includes: an X-ray source; an input unit configured to receive an input of distance information between the X-ray source and an X-ray detector; a reference light emitter configured to irradiate a light from the X-ray source to a direction in which the X-ray detector is placed; at least one auxiliary light emitter provided apart from the reference light emitter by a predetermined distance and configured to irradiate a light to be overlapped with a light from the reference light emitter in a predetermined distance; and a controller configured to determine an auxiliary light emitter corresponding to the input distance information among the at least one auxiliary light emitter when the distance information is input, and configured to control the reference light emitter and the determined auxiliary light emitter so that the reference light emitter and the determined auxiliary light emitter irradiate a light.

The at least one auxiliary light emitter is provided such that a light irradiated from the reference light emitter and a light irradiated from the at least one auxiliary light emitter have a predetermined angle.

When the distance information is input, the controller turns on the reference light emitter and an auxiliary light emitter corresponding to the input distance information so that the reference light emitter and the auxiliary light emitter irradiate a light.

A light irradiated from the reference light emitter and a light irradiated from the at least one auxiliary light emitter are overlapped and coincided as a single line to form an overlapped line in the predetermined distance.

The reference light emitter and the at least one auxiliary light emitter are provided adjacent to the X-ray source to face the X-ray imaging apparatus.

The reference light emitter and the at least one auxiliary light emitter comprises Light Emitting Diode (LED) or Light Amplification by Simulated Emission of Radiation (LASER) diode.

The X-ray source is provided to be movable so that the overlapped line is placed on the X-ray detector.

A storage configured to store distance information between the X-ray source and the X-ray detector.

The storage stores a corresponding relation between the stored distance information and the at least one auxiliary light emitter.

In accordance with another aspect of the present disclosure, an X-ray imaging apparatus includes: an X-ray source; an input unit configured to receive an input of distance information between the X-ray source and an X-ray detector; a reference light emitter configured to irradiate a light from the X-ray source to a direction in which the X-ray detector is placed; an angle adjustment light emitter configured to adjust an irradiation of a light to irradiate a light capable of being overlapped with a light irradiated from the reference light emitter in the input distance; and a controller configured to adjust an irradiation angle of a light of the angle adjustment light emitter when the distance information is input, and configured to control the reference light emitter and the angle adjustment light emitter so that the reference light emitter and the angle adjustment light emitter irradiate a light.

The angle adjustment light emitter comprises a first driving motor configured to rotate the angle adjustment light emitter.

When the distance information is input, the controller adjusts an irradiation angle of a light of the angle adjustment light emitter so that a light capable of being overlapped with a light irradiated from the reference light emitter in the input distance is irradiated.

A light irradiated from the reference light emitter and a light irradiated from the angle adjustment light emitter are overlapped and coincided as a single line to form an overlapped line in the predetermined distance.

In accordance with another aspect of the present disclosure, an X-ray imaging apparatus includes: an X-ray source; an input unit configured to receive an input of distance information between the X-ray source and an X-ray detector; a reference light emitter configured to irradiate a light from the X-ray source to a direction in which the X-ray detector is placed; at least one auxiliary light emitter configured to irradiate a light; a light reflector provided apart from the at least one auxiliary light emitter by a predetermined distance and configured to reflect a light irradiated from the at least one auxiliary light emitter; and a controller configured to adjust a reflection angle of a light of the light reflector when the distance information is input, and configured to control the reference light emitter and the at least one auxiliary light emitter so that the reference light emitter and the at least one auxiliary light emitter irradiate a light.

The light reflector adjusts a reflection angle of a light so that a light irradiated from the reference light emitter and the reflected light are overlapped in the input distance.

The light reflector comprises a second driving motor configured to rotate the light reflector.

In accordance with another aspect of the present disclosure, a method for controlling an X-ray imaging apparatus provided with a reference light emitter and at least one light emitter includes: receiving an input of distance information between an X-ray source and an X-ray detector; determining an auxiliary light emitter corresponding to the input distance information among the at least one light emitters when the distance information is input; and controlling the reference light emitter and the determined auxiliary light emitter so that the reference light emitter and the determined auxiliary light emitter irradiate a light.

In accordance with another aspect of the present disclosure, a method for controlling an X-ray imaging apparatus provided with a reference light emitter and an angle adjustment light emitter includes: receiving an input of distance information between an X-ray source and an X-ray detector; adjusting an irradiation angle of a light of the angle adjustment light emitter so that a light, which is capable of being overlapped with a light irradiated from the reference light emitter in the input distance, is irradiated; and controlling the reference light emitter and the angle adjustment light emitter so that the reference light emitter and the angle adjustment light emitter irradiate a light.

In accordance with another aspect of the present disclosure, a method for controlling an X-ray imaging apparatus provided with a reference light emitter, at least one auxiliary light emitter and a light reflector includes: receiving an input of distance information between an X-ray source and an X-ray detector; adjusting a reflection angle of a light of the light reflector; irradiating a light by the reference light emitter and the at least one auxiliary light emitter; and reflecting a light, which is irradiated from the at least one auxiliary light emitter, by the light reflector.

Before undertaking the DETAILED DESCRIPTION below, it may be advantageous to set forth definitions of certain words and phrases used throughout this patent document: the terms "include" and "comprise," as well as derivatives thereof, mean inclusion without limitation; the term "or," is inclusive, meaning and/or; the phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like; and the term "controller" means any device, system or part thereof that controls at least one operation, such a device may be implemented in hardware, firmware or software, or some combination of at least two of the same. It should be noted that the functionality associated with any particular controller may be centralized or distributed, whether locally or remotely. Definitions for certain words and phrases are provided throughout this patent document, those of ordinary skill in the art should understand that in many, if not most instances, such definitions apply to prior, as well as future uses of such defined words and phrases.

BRIEF DESCRIPTION OF THE DRAWINGS

For a more complete understanding of the present disclosure and its advantages, reference is now made to the following description taken in conjunction with the accompanying drawings, in which like reference numerals represent like parts.

DETAILED DESCRIPTION

Figure 1:
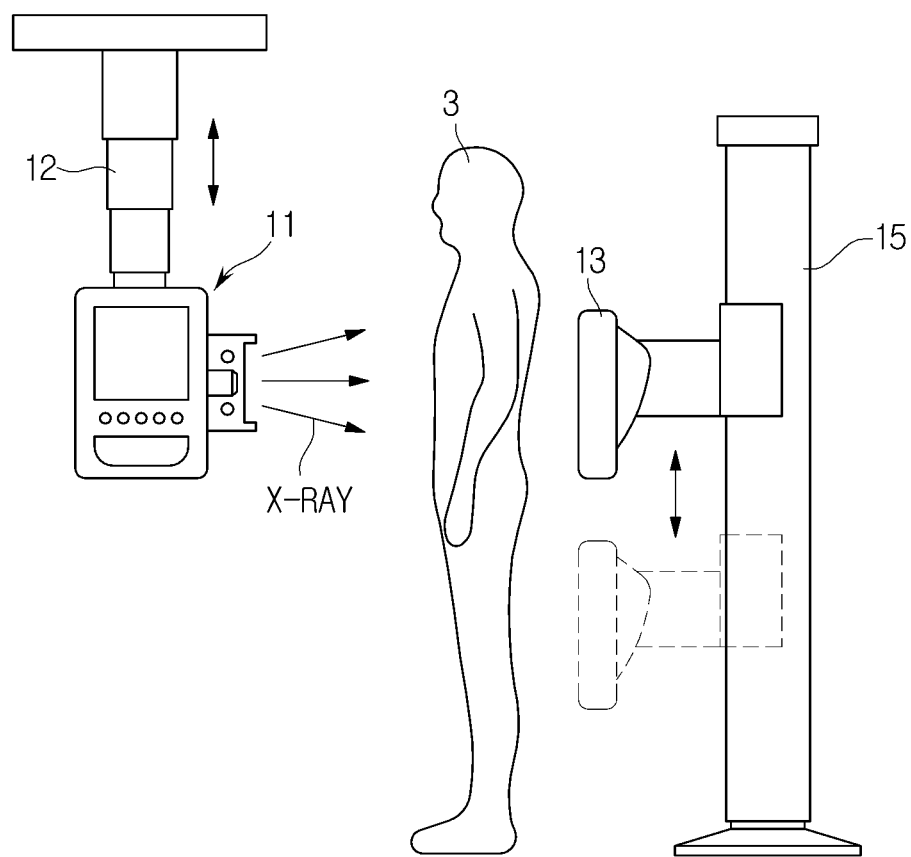
FIG. 1 illustrates an exterior view of a stationary X-ray imaging apparatus.

FIGS. 1 through 25, discussed below, and the various embodiments used to describe the principles of the present disclosure in this patent document are by way of illustration only and should not be construed in any way to limit the scope of the disclosure. Those skilled in the art will understand that the principles of the present disclosure may be implemented in any suitably arranged medical imaging device.

The present disclosure will now be described more fully with reference to the accompanying drawings, in which exemplary embodiments of the disclosure are shown.

Embodiments disclosed in the present disclosure and configurations illustrated in drawings are merely preferable examples of the present disclosure. It should be understood that various modifications replaceable to the embodiments and the drawings of the present disclosure are available at the application time of the present application.

The present disclosure and methods of accomplishing the same may be understood more readily by reference to the following detailed description of embodiments and the accompanying drawings. However, the present disclosure may be embodied in many different forms, and should not be construed as being limited to the embodiments set forth herein. Rather, these embodiments are provided so that this disclosure will be through and complete and will fully convey the concept of the disclosure to those skilled in the art, and the present disclosure will only be defined by the appended claims.

The terminology used herein will be described briefly, and the present disclosure will be described in detail.

The terminology used herein is defined in consideration of the function of corresponding components used in the present disclosure and may be varied according to users, operator's intention, or practices. In addition, an arbitrary defined terminology may be used in a specific case and will be described in detail in a corresponding description paragraph. Therefore, the terminology used herein is for the purpose of describing particular embodiments only and is not intended to be limiting of the disclosure.

When a part "includes" or "comprises" an element, unless there is a particular description contrary thereto, the part can further include other elements, not excluding the other elements. In the following description, terms such as "part", "module" and "unit" indicate a unit for processing at least one function or operation, wherein the unit and the block may be embodied as software or hardware, such as Field Programmable Gate Array (FPGA), Application Specific Integrated Circuit (ASIC), or embodied by combining hardware and software. However, the term "part" "module" and "unit" are not limited to software or hardware. Further, "part" "module" and "unit" may be constructed to exist in an addressable storage module, or to play one or more processors. "part" "module" and "unit" includes elements (e.g., software elements, object-oriented software elements, class elements and task elements), processors, functions, properties, procedures, sub-routines, segments of a program code, drivers, firmware, a microcode, a circuit, data, a database, data structures, tables, arrays, and variables. The function provided in the components and "part" may be combined into fewer components and "part" or further separated into additional components and the "part".

In the following detailed description, only certain exemplary embodiments of the present disclosure have been shown and described, simply by way of illustration. The drawings and description are to be regarded as illustrative in nature and not restrictive.

Hereinafter the term of "user" may represent medical professional, such as a doctor, a nurse, a medical technologist, a medical imaging specialists, a technician to service for the medical device, but is not limited thereto.

Figure 2A:
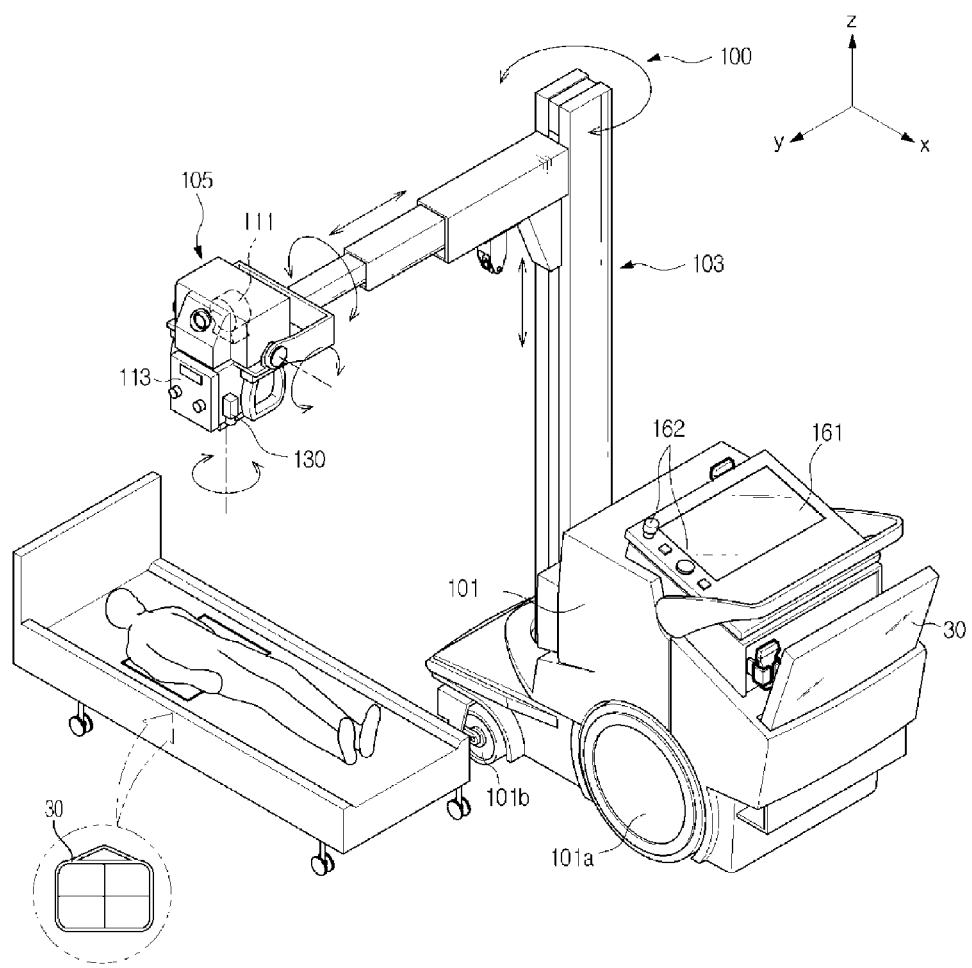
FIG. 2A illustrates an exterior view of a mobile X-ray imaging apparatus in accordance with an embodiment.
Figure 2B:
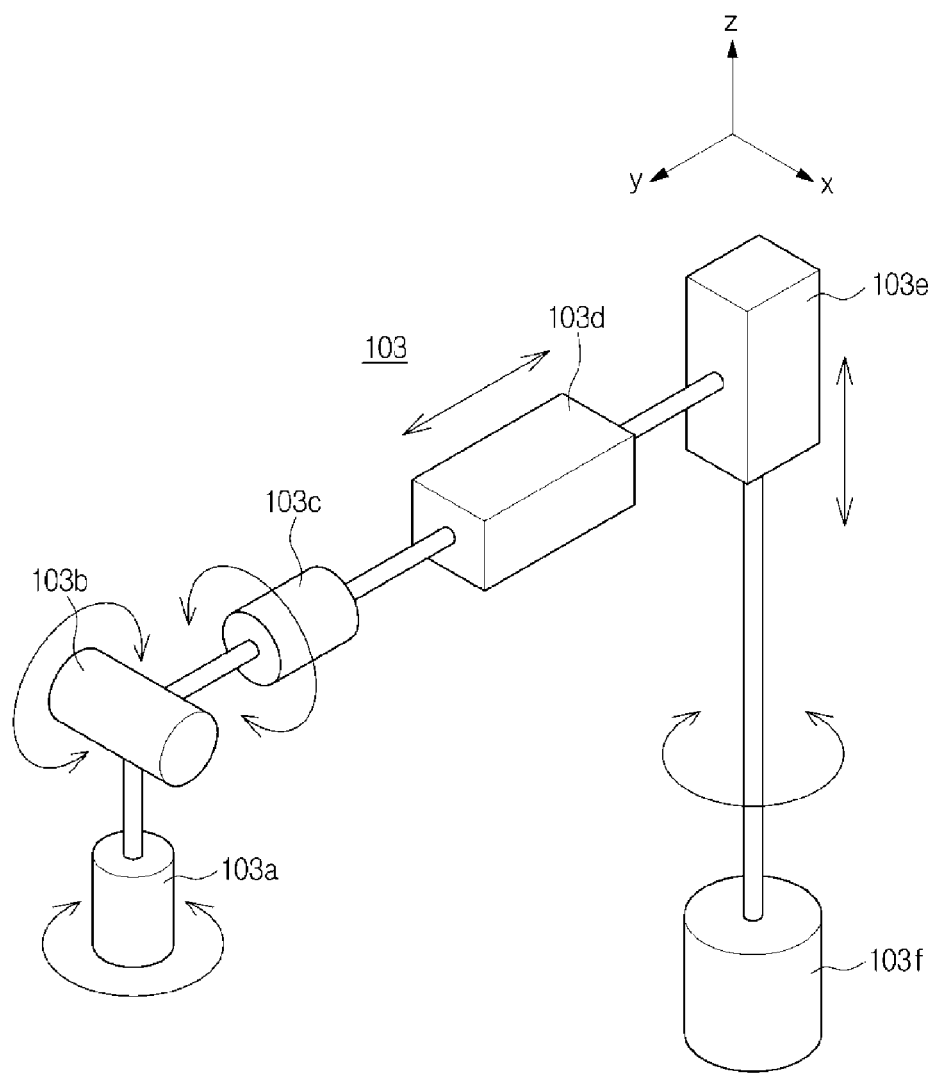
FIG. 2B illustrates a plurality of auxiliary-arms forming a tube arm of mobile X-ray imaging apparatus in accordance with an embodiment.

FIG. 1 illustrates an exterior view of a stationary X-ray imaging apparatus 10. FIG. 2A illustrates an exterior view of a mobile X-ray imaging apparatus 100 in accordance with an embodiment, and FIG. 2B illustrates a view illustrating a plurality of auxiliary-arms forming a tube arm 103 of mobile X-ray imaging apparatus 100 in accordance with an embodiment.

In an X-ray imaging apparatus of FIG. 1, an X-ray source 11 and an X-ray detector 13 may be fixed to a certain space. For example, as illustrated in FIG. 1, the X-ray source 11 may be connected to an arm 12 mounted to a wall of an examination room, and the X-ray detector 13 may be connected to a housing 15 fixed to a floor of the examination room. The X-ray source 11 that is configured to allow the arm 12 connected to the X-ray source 11 to be extended may be movable in a vertical direction about the ground, and the X-ray detector 13 may be also movable in a vertical direction along the housing 15. That is, the X-ray imaging apparatus 10 may include the X-ray source 11 and the X-ray detector 13 wherein the X-ray source 11 and the X-ray detector 13 are moved in a predetermined direction in a predetermined certain space relative to a patient 3.

However, as illustrated in FIG. 2A, a mobile X-ray imaging apparatus 100 may be provided with an X-ray source 105 and an X-ray detector 30, wherein the X-ray source 105 and the X-ray detector 30 may be free to move in any direction in a three-dimensional space.

Referring to FIG. 2A, the mobile X-ray imaging apparatus 100 may be implemented to be mobile. Particularly, an X-ray source 105 may include an X-ray tube 111 and a collimator 113, and the X-ray source 105 may be supported by a tube arm 103 connected to a mobile body 101.

The collimator 113 may be placed in a front of a window of the X-ray tube 111 to adjust a radiation field of X-rays. Since scattered X-rays may be reduced when the radiation field of X-rays is reduced, an optimal radiation field of X-rays may be determined based on information, e.g. a distance and a relative angle between the X-ray tube 111 and the X-ray detector 30.

Although not shown in FIG. 2A, a display panel (not shown) including a touch pad may be mounted to a position adjacent to the collimator 113, and a user may input a command related to various control flows of the mobile X-ray imaging apparatus 100 by touching the display panel (not shown). In addition, a reference light emitter and at least one auxiliary light emitter in accordance with an embodiment of the present disclosure may be provided in the display panel (not shown).

In the mobile body 101, a wheel 101a and 101b may be mounted to allow the mobile X-ray imaging apparatus 100 to be free to move, and a display 161 configured to display a screen related to a control of the mobile X-ray imaging apparatus 100 and an input unit 162 configured to receive an input of a user's control command may be provided.

The display 161 may be implemented by at least one of various display devices, e.g. Liquid Crystal Display (LCD), Light Emitting Diode (LED), Organic Light Emitting Diode (OLED), Plasma Display Panel (PDP), and Cathode-Ray Tube (CRT), and the input unit 162 may be implemented by at least one of a key board, a mouse, a track ball, and a touch pad.

The X-ray detector 30 may be implemented in a portable type that is separately formed from the mobile X-ray imaging apparatus 100. However, for convenience in movement, a holder may be formed in the mobile body 101 of the mobile X-ray imaging apparatus 100 so that the X-ray detector 30 may be accommodated in the holder.

An imaging unit 130 may be implemented by a camera, e.g. a CCD camera or a CMOS camera. In addition, the imaging unit 130 may record a still image and a video image. The imaging unit 130 may record an object in real time, and a recorded image may be transmitted to a controller 150 or displayed on the display 161 in real time.

For example, the imaging unit 130 may be mounted to the X-ray source 105. However, if an initial relative position of the imaging unit 130 and the X-ray tube 111 are pre-determined, there may be no limitation in the position of the imaging unit 130. The X-ray tube 111 may be movable according to the movement of the tube arm 103 and the tube arm 103 may be configured to have a high degree of freedom by being formed by a plurality of auxiliary arms.

As illustrated in FIG. 2B, the tube arm 103 may include six auxiliary arms. A three dimensional space in which the mobile X-ray imaging apparatus 100 is placed may be defined by an X-axis, a Y-axis, and a Z-axis. Therefore, due to a rotation movement or a linear movement of the auxiliary arms, the X-ray tube 111 may perform a rotation movement, e.g. a yaw motion, a pitch motion and a roll motion, and a linear movement in the X-axis, Y-axis, and Z-axis, based on a body coordinate system or an absolute coordinate system based on the movement of the tube arm 103. Meanwhile, a roll angle, a pitch angle, and a yaw angle which are a relative angle according to the body coordinate system may be converted into a roll angle, a pitch angle, and a yaw angle which are an absolute angle according to the absolute coordinate system. In a stationary X-ray imaging apparatus 10, an axis of the absolute coordinate system may be placed in a fixed portion of the stationary X-ray imaging apparatus 10, and in the mobile X-ray imaging apparatus 100, an axis of the absolute coordinate system may be placed in a portion of a body connected to a tube arm 103 of the mobile X-ray imaging apparatus 100. In addition, in both of the stationary X-ray imaging apparatus 10 and the mobile X-ray imaging apparatus 100, the axis of the absolute coordinate system may be placed in a portion of an X-ray detector. In embodiments of the mobile X-ray imaging apparatus 100, any one of the body coordinate system and the absolute coordinate system may be allowed to be used, but the aforementioned embodiment will be described according to the body coordinate system.

According to the body coordinate system, a first auxiliary arm 103a may be connected to the X-ray source 105 to perform a rotation motion with respect to the Z-axis (a yaw motion), and a second auxiliary arm 103b may connect the first auxiliary arm 103a to a third auxiliary arm 103c to perform a rotation motion with respect to the X-axis (a pitch motion). In addition, the third auxiliary arm 103c may connect the second auxiliary arm 103b to a fourth auxiliary arm 103d to perform a rotation motion with respect to the Y-axis (a roll motion), and the fourth auxiliary arm 103d may connect the third auxiliary arm 103c to a fifth auxiliary arm 103e to perform a linear movement in the Y-axis. In addition, a sixth auxiliary arm 103f may be connected to the mobile body 101 to perform a rotation motion with respect to the Z-axis (a yaw motion), and the fifth auxiliary arm 103e may connect the sixth auxiliary arm 103f to the fourth auxiliary arm 103d to perform a linear movement in the Z-axis.

Meanwhile, an orientation of the X-ray tube 111 may be controlled by the yaw motion of the first auxiliary arm 103a, the pitch motion of the second auxiliary arm 103b and the roll motion of the third auxiliary arm 103c. The orientation of the X-ray tube 111 may represent a direction to which the X-ray tube 111 faces, a direction of X-ray beam irradiated from the X-ray tube 111, or a relative angle between the X-ray tube 111 and an X-ray detector 30. In addition, the position of the X-ray tube 111 may be controlled by the linear movement of the fourth auxiliary arm 103d in the Y-axis, the linear movement of the fifth auxiliary arm 103e in the Z-axis, the yaw motion of the sixth auxiliary arm 103f.

Therefore, by the tube arm 103 forming six auxiliary arms, the X-ray tube 111 may be placed in any position in the three dimensional space. In this time, the position of the X-ray tube 111 may be automatically controlled by the controller 150, or alternatively, the position of the X-ray tube 111 may be semi-automatically controlled since a part of control is manually performed by a user's operation.

Figure 3:
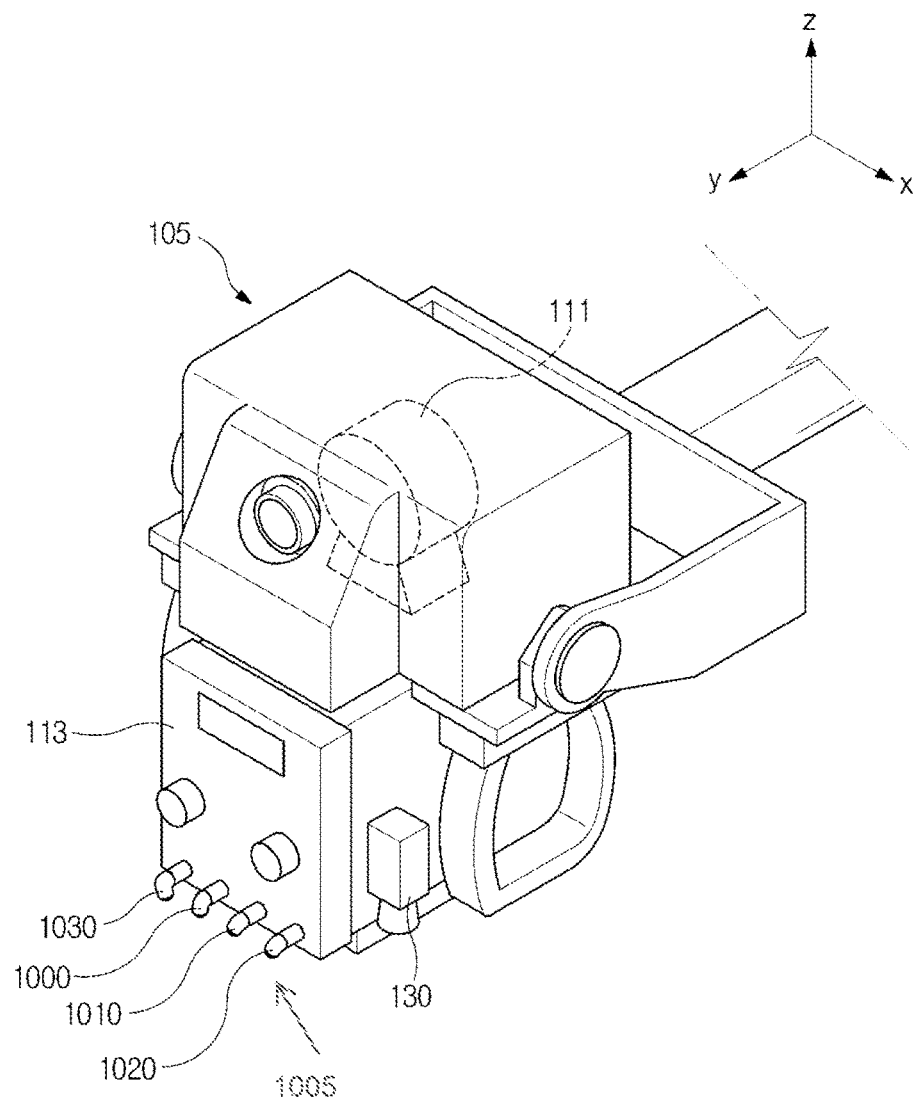
FIG. 3 illustrates a schematic view of a reference light emitter and at least one auxiliary light emitters provided in an X-ray source in accordance with an embodiment of the present disclosure.

FIG. 3 illustrates a schematic view of a reference light emitter 1000 and at least one auxiliary light emitter 1005 provided in an X-ray source 105 in accordance with an embodiment of the present disclosure.

Referring to FIG. 3, the X-ray source 105 of the X-ray imaging apparatus 100 may include a reference light emitter 1000 and at least one auxiliary light emitter 1005 wherein the auxiliary light emitter 1005 may include a first auxiliary light emitter 1010, a second auxiliary light emitter 1020, and a third auxiliary light emitter 1030. To describe an embodiment of the present disclosure, a mobile X-ray imaging apparatus 100 including a single reference light emitter 1000 and three auxiliary light emitters 1005 is described as an example, but there is no limitation in the number of auxiliary light emitters.

As illustrated in FIG. 3, the reference light emitter 1000, the first auxiliary light emitter 1010, the second auxiliary light emitter 1020, and the third auxiliary light emitter 1030 may be provided in the collimator 113, but there may be no limitation in a position in which the reference light emitter 1000, the first auxiliary light emitter 1010, the second auxiliary light emitter 1020, and the third auxiliary light emitter 1030 are installed, as long as being adjacent to the X-ray source 105 and configured to emit a light to a direction of an object. As mentioned above, although not shown in FIG. 3, a display panel (not shown) including a touch pad may be provided adjacent to the collimator 113 and the reference light emitter 1000, the first auxiliary light emitter 1010, the second auxiliary light emitter 1020, and the third auxiliary light emitter 1030 may be provided in a front surface of the display panel.

The reference light emitter 1000, the first auxiliary light emitter 1010, the second auxiliary light emitter 1020, and the third auxiliary light emitter 1030 may be apart a predetermined distance from each other, as illustrated in FIG. 3, wherein the predetermined distance may be determined according to whether a light irradiated from the reference light emitter 1000 and a light irradiated from the auxiliary light emitter 1005 are overlapped when the reference light emitter 1000 and the at least one auxiliary light emitter 1005 are installed, but there may be no limitation in the predetermined distance.

The reference light emitter 1000 and the at least one auxiliary light emitter 1005 may include a light source configured to irradiate a light and a wide-angle lens configured to diffuse an irradiated light to a perpendicular direction with respect to a direction in which an object is placed.

The light emitter may employ Light Emitting Diode (LED) or Light Amplification by Simulated Emission of Radiation (LASER) diode configured to irradiate a light in various direction. That is, a light having a wavelength may be irradiated from the light emitter wherein the light is identified with naked eyes, e.g. a laser or a visible ray, and a user may recognize a position where the irradiated light reaches with naked eyes.

The wide-angle lens may be formed of a material transmitting a light, and configured to diffuse a light irradiated from the light emitter to a perpendicular direction with respect to a direction, in which an object is placed, to have a fan shape by using refraction and total reflection (hereinafter a light that is diffused in a direction of an object to have a fan shape is referred to as a flat light).

Figure 4:
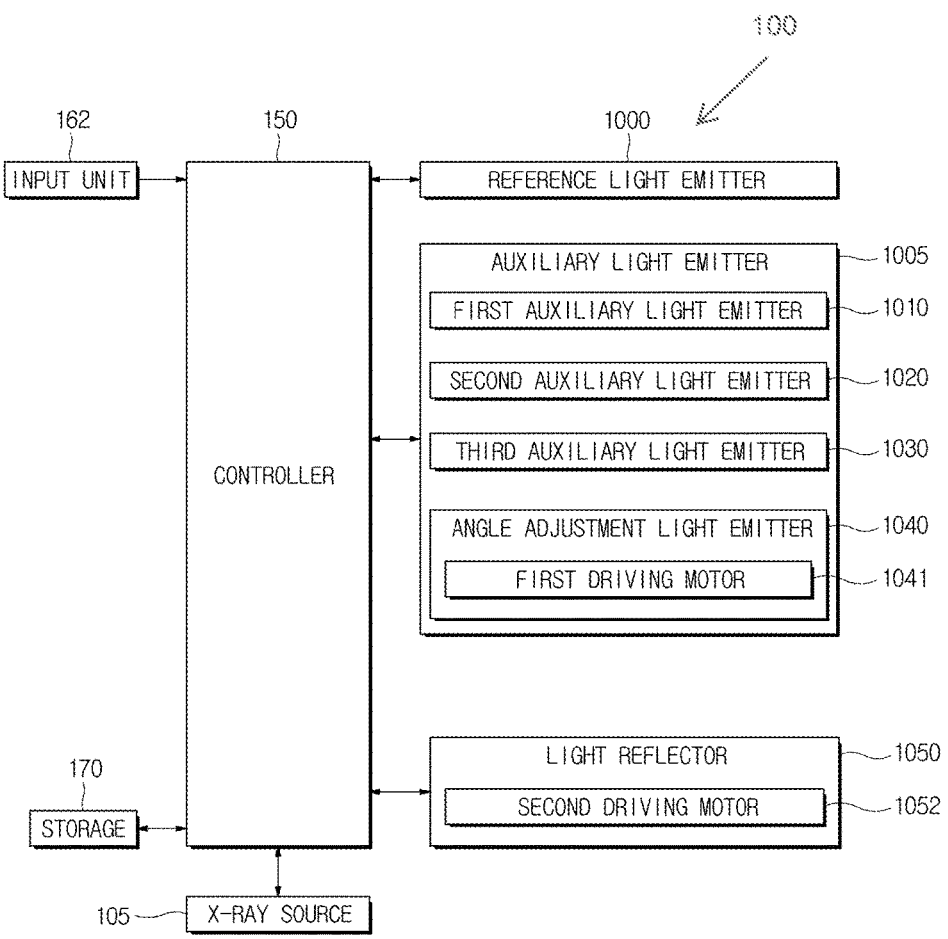
FIG. 4 illustrates a control block diagram of an X-ray imaging apparatus in accordance with an embodiment of the present disclosure.

FIG. 4 illustrates a control block diagram of a mobile X-ray imaging apparatus 100 in accordance with an embodiment of the present disclosure.

Referring to FIG. 4, according to an embodiment, the mobile X-ray imaging apparatus 100 may include an X-ray source 105, a controller 150, an input unit 162, a storage 170, a reference light emitter 1000, at least one auxiliary light emitter 1005, and a light reflector 1050.

The at least one auxiliary light emitter 1005 may include the first auxiliary light emitter 1010, the second auxiliary light emitter 1020, the third auxiliary light emitter 1030, and an angle adjustment light emitter 1040, wherein the angle adjustment light emitter 1040 may include a first driving motor 1041. In addition, the light reflector 1050 may include a second driving motor 1052.

The X-ray source 105 may generate X-rays by receiving a power to record an object by emitting X-rays to the object. As for the X-ray source 105, energy of X-rays may be controlled by a tube voltage, and the intensity and a dose of X-rays may be controlled by a tube current and an expose time of X-ray.

The input unit 162 may receive an input of a control command related to an operation of the mobile X-ray imaging apparatus 100 and an input of a variety of information related to an X-ray imaging, and may provide an interface configured to receive an input of a manipulation and a control command related to each devices. In addition, the input unit 162 may receive an input of distance information between the X-ray source 105 and the X-ray detector 30. The distance information between the X-ray source 105 and the imaging unit 130 may correspond to information related to a distance between the reference light emitter 1000 that is adjacent to the X-ray source 105 and the X-ray detector 30.

When performing an X-ray imaging of an object, a distance between the X-ray source 105 and the X-ray detector 30 may be defined as "source-image distance (SID)" wherein the SID value may vary according to the type or a target part of an object of X-ray imaging.

A reference unit of the SID may typically include 100 cm, 130 cm, and 180 cm and it may represent that the X-ray detector 30 is needed to be placed in a position apart from the X-ray source 105 by 100 cm, 130 cm, and 180 cm according to the type or a target part of X-ray imaging object. Hereinafter for a convenience of description to describe a mobile X-ray imaging apparatus 100 and a control method thereof in accordance with an embodiment, a case in which SID value corresponds to 100 cm, 130 cm, and 180 cm will be described as an example, but the SID value is not limited thereto. When performing an X-ray imaging of an object in a position where does not correspond to the SID reference value, there may be a risk of excessive exposure to the object.

Therefore, prior to performing an X-ray imaging of an object, a position of the X-ray source 105 may be adjusted so that a distance between the mobile X-ray imaging apparatus 100 and the X-ray detector 30 corresponds to the reference SID. In order to manually adjust the distance between the X-ray source 105 and the X-ray detector 30, a user needs to estimate whether a distance between the X-ray source 105 and the X-ray detector 30 corresponds to the reference SID value with a measure tape or with a rough guess, but the method may cause a reduction of user's convenience or an inaccuracy of the measurement.

Therefore, according to an embodiment, when a user selects pre-stored information related to a distance between the X-ray source 105 and the X-ray detector 30, the mobile X-ray imaging apparatus 100 may display the distance information corresponding to user's selection to allow a user to intuitively recognize the distance information.

A user may input a SID value between the X-ray source 105 and the X-ray detector 30 via the input unit 162. That is, the user may directly input the reference SID value by using at least one of a key board, a mouse, a track ball, and a touch pad, or by touching a button in which the reference SID value is set.

The controller 150 may overall control of a control flow related to an operation of the mobile X-ray imaging apparatus 100. The controller 150 may perform an X-ray imaging of an object by controlling the X-ray source 105, and may determine an auxiliary light emitter 1005 corresponding to the distance information between the X-ray source 105 and the imaging unit 130, which is input from a user according to an embodiment. The controller 150 may control the reference light emitter 1000 and the auxiliary light emitter 1005 so that the reference light emitter 1000 and the auxiliary light emitter 1005 irradiate a light, and the controller 150 may control the first auxiliary light emitter 1010, the second auxiliary light emitter 1020, and the third auxiliary light emitter 1030 included in the auxiliary light emitter 1005, and the angle adjustment light emitter 1040, respectively.

The controller 150 may control the first driving motor 1041 included in the angle adjustment light emitter 1040 to adjust an irradiation angle of a light of the angle adjustment light emitter 1040, and the controller 150 may control the second driving motor 1052 included in the light reflector 1050 to adjust an angle of a light that is reflected by the light reflector 1050.

The controller 150 may include a single general processor configured to perform all calculations related to an operation of the mobile X-ray imaging apparatus 100, or a processor configured to perform a calculation specialized in a communication, e.g. a communication processor configured to perform a calculation related to the communication, and a control, e.g. a control processor configured to perform a calculation related to a control operation.

The storage 170 may store distance information between the X-ray source 105 and the X-ray detector 30. Particularly, as mentioned above, the distance information between the X-ray source 105 and the X-ray detector 30 may correspond to SID information of 100 cm, 130 cm and 180 cm, and the reference SID value may be stored in the storage 170.

In addition, information of the auxiliary light emitter 1005 corresponding to the reference SID value may be stored in the storage 170. That is, information corresponding to the SID value such as 100 cm, 130 cm, and 180 cm may be stored, and thus among the first auxiliary light emitter 1010, the second auxiliary light emitter 1020, and the third auxiliary light emitter 1030, the auxiliary light emitter 1005 corresponding to distance information that is input from a user may be turned on.

The storage 170 may store angle information that allows an angle of the angle adjustment light emitter 1040 or the light reflector 1050 to be adjusted based on distance information between the X-ray source 105 and the X-ray detector 30. That is, the storage 170 may store angle information to adjust an angle of the angle adjustment light emitter 1040 so that a light irradiated from the reference light emitter 1000 and a light irradiated from the angle adjustment light emitter 1040 are overlapped with each other in a position corresponding to a distance that is input when distance information is input from a user. In addition, the storage 170 may store angle information to adjust an angle of the light reflector 1050 to reflect a light so that the light is overlapped with a light irradiated from the reference light emitter 1000 in the position corresponding to the distance input.

The storage 170 may store a program that is needed to analyze a variety of data and an examination medium. The storage 170 may include at least one type of storage media, e.g. a flash memory type, a hard disk type, a multimedia card micro type, a card type memory, such as SD and XD memory, a random access memory (RAM), a static random access memory (SRAM), a read-only memory (ROM), an electrically erasable programmable read-only memory (EE-PROM), a programmable read-only memory (PROM), a magnetic memory, a magnetic disk, and an optical disk.

As illustrated in FIG. 3, according to an embodiment, the reference light emitter 1000 may be provided in the collimator 113 to irradiate a light from the X-ray source 105 to a direction in which the X-ray detector 30 is placed. There may be no limitation in the position of the reference light emitter 1000 as long as being adjacent to the X-ray source 105 and being allowed to irradiate a light to a direction of the X-ray detector 30.

The first auxiliary light emitter 1010, the second auxiliary light emitter 1020, and the third auxiliary light emitter 1030 may be provided in the collimator 113 to irradiate a light to be overlapped with a light irradiated from the reference light emitter 1000. In this case, a position in which the lights are overlapped may be a position apart from the X-ray source 105 by a SID value, which is input via the input unit 162.

The first auxiliary light emitter 1010, the second auxiliary light emitter 1020, and the third auxiliary light emitter 1030 may be apart from the reference light emitter 1000 by a pre-determined distance while having a predetermined angle with the reference light emitter 1000 in the Z axis direction. The predetermined angle may represent a certain angle of a light emitter of the first auxiliary light emitter 1010, the second auxiliary light emitter 1020, and the third auxiliary light emitter 1030 to allow a light irradiated from the first auxiliary light emitter 1010, the second auxiliary light emitter 1020, and the third auxiliary light emitter 1030 to be overlapped with a light irradiated from the reference light emitter 1000 in a position corresponding to a distance that is input.

The angle adjustment light emitter 1040 may be provided apart from the reference light emitter 1000 by a predetermined distance, and may adjust an irradiation angle of a light by including the first driving motor 1041. Particularly, based on a distance between the X-ray source 105 and the X-ray detector 30 that is input from a user, the angle adjustment light emitter 1040 may adjust an irradiation angle of a light so that the light is overlapped with a light irradiated from the reference light emitter 1000. That is, the first driving motor 1041 may be rotated by a pre-set angle and thus the angle adjustment light emitter 1040 may irradiate a light in a setting angle.

The first auxiliary light emitter 1010, the second auxiliary light emitter 1020, and the third auxiliary light emitter 1030 may be provided to have a predetermined angle with the reference light emitter 1000 to irradiate a light that is overlapped with a light irradiated from the reference light emitter 1000 according to a SID value and but, in the angle adjustment light emitter 1040, an irradiation angle of a light may vary by the first driving motor 1041.

The light reflector 1050 may be apart from the reference light emitter 1000 and the at least one auxiliary light emitter 1005 by a predetermined distance, and the light reflector 1050 may reflect a light irradiated from the at least one auxiliary light emitter 1005 by including the second driving motor 1052. Particularly, the at least one auxiliary light emitter 1005 may be installed in a direction to irradiate a light to the light reflector 1050, and in the light reflector 1050, a reflection angle of a light may vary by the second driving motor 1052. That is, the light reflector 1050 may change a path of a light that is reflected so that a light irradiated from the auxiliary light emitter 1005 is overlapped with a light irradiated from the reference light emitter 1000 based on SID information that is input from a user.

The first driving motor 1041 and the second driving motor 1052 may rotate the angle adjustment light emitter 1040 and the light reflector 1050, respectively, under a control of the controller 150.

As mentioned above, a light emitter of the reference light emitter 1000 and the at least one auxiliary light emitter 1005 may employ Light Emitting Diode (LED) or Light Amplification by Simulated Emission of Radiation (LASER) diode configured to irradiate a light in various direction. That is, a light having a wavelength may be irradiated from the light emitter wherein the light is identified with naked eyes, e.g. a laser or a visible ray, and a user may recognize a location where the irradiated light reaches with naked eyes. A light emitter of the reference light emitter 1000 and the at least one auxiliary light emitter 1005 may irradiate a flat light having a fan shape in a direction in which the X-ray detector 30 is placed, or irradiate a light having a square or circular shape. There may be a variety of embodiments in the shapes of light irradiated from a light source.

Hereinafter a variety of embodiments will be described in details with reference to FIGS. 5 to 20.

Figure 5:
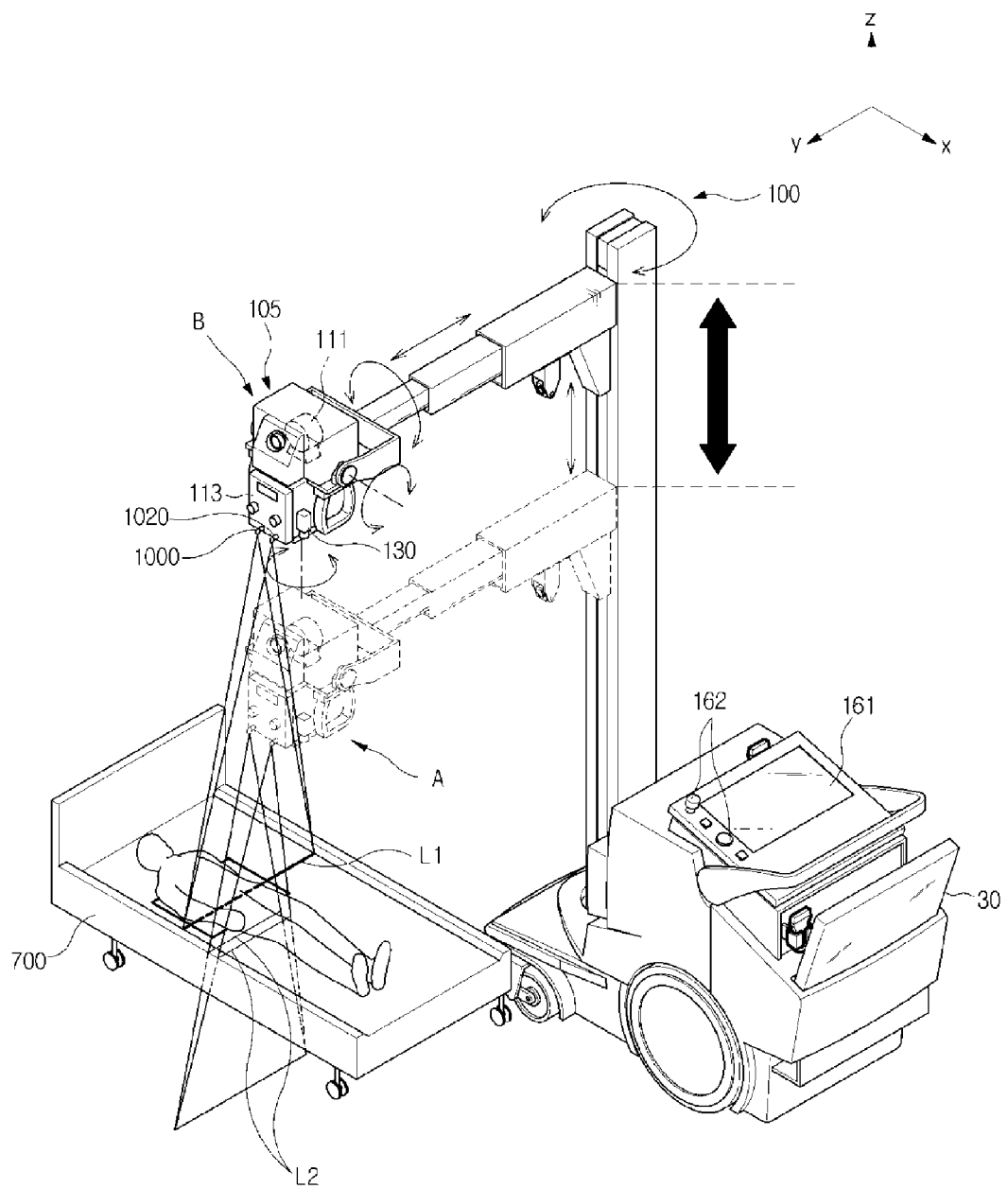
FIG. 5 illustrates a schematic view of a position in which a light irradiated from a reference light emitter and a light irradiated from an auxiliary light emitter are overlapped in accordance with an embodiment of the present disclosure.

FIG. 5 illustrates a schematic view of a position in which a light irradiated from a reference light emitter 1000 and a light irradiated from a second auxiliary light emitter 1020 are overlapped in accordance with an embodiment of the present disclosure.

For convenience of description, in FIG. 5, a case in which a light irradiated from the reference light emitter 1000 and a light irradiated from the second auxiliary light emitter 1020 are overlapped, is described as an example.

As illustrated in FIG. 5, the reference light emitter 1000 and the second auxiliary light emitter 1020 may irradiate a light to a direction in which the X-ray detector 30 is placed. An object may be placed in a patient table 700, and the reference light emitter 1000 and the second auxiliary light emitter 1020 may irradiate a flat light that is diffused to have a fan shape at a right angle to a direction in which the object is placed.

The second auxiliary light emitter 1020 may be provided to have a predetermined angle with respect to the reference light emitter 1000, and thus a flat light irradiated from the reference light emitter 1000 and a flat light irradiated from the second auxiliary light emitter 1020 may be overlapped in a predetermined distance.

When a user inputs distance information between the X-ray source 105 and the X-ray detector 30 via the input unit 162, the controller 150 (FIG. 4) may determine the second auxiliary light emitter 1020 corresponding to the input distance information, and when the second auxiliary light emitter 1020 is determined, a position in which a light irradiated from the reference light emitter 1000 and a light irradiated from the second auxiliary light emitter 1020 are overlapped, may be determined. Therefore, the user may confirm whether the X-ray source 105 is placed in a position corresponding to the input distance information, by checking a position in which the light irradiated from the reference light emitter 1000 and the light irradiated from the second auxiliary light emitter 1020 are overlapped.

Referring to FIG. 5, a distance from the reference light emitter 1000 to a position in which a light irradiated from the reference light emitter 1000 and a light irradiated from the second auxiliary light emitter 1020 are overlapped when the X-ray source 105 is placed in a position (A) may be the same as a distance from the reference light emitter 1000 to a position in which a light irradiated from the reference light emitter 1000 and a light irradiated from the second auxiliary light emitter 1020 are overlapped when the X-ray source 105 is placed in a position (B). However, a height of the position in which the light irradiated from the reference light emitter 1000 and the light irradiated from the second auxiliary light emitter 1020 are overlapped when the X-ray source 105 is placed in a position (A) may be different from a height of the position in which the light irradiated from the reference light emitter 1000 and the light irradiated from the second auxiliary light emitter 1020 are overlapped when the X-ray source 105 is placed in a position (B). Accordingly, a user may allow the position in which lights are overlapped to be identical to the position of the X-ray detector 30 by confirming a position in which lights are overlapped and by adjusting the height of the X-ray source 105.

As illustrated in FIG. 5, when the X-ray source 105 is placed in the position (A), a light irradiated from the reference light emitter 1000 and a light irradiated from the second auxiliary light emitter 1020 may be overlapped under the patient table 700 in which the X-ray detector 30 is placed. That is, in the patient table 700, the light irradiated from the reference light emitter 1000 and the light irradiated from the second auxiliary light emitter 1020 may be not displayed in a single line in which the lights are overlapped, but the lights may be displayed in two lines (L2).

Therefore, when the X-ray source 105 is placed in the position (A), a distance between the X-ray source 105 and the X-ray detector 30 may be shorter than distance information input from a user, and thus the user may maintain a predetermined distance between the X-ray source 105 and the X-ray detector 30 by moving the X-ray source 105 along the Z axis direction.

When the X-ray source 105 is placed in the position (B), a light irradiated from the reference light emitter 1000 and a light irradiated from the second auxiliary light emitter 1020 may be overlapped on the patient table 700 in which the X-ray detector 30 is placed and the lights may be displayed in an overlapped line (L1). That is, since a distance between the reference light emitter 1000 and the overlapped line (L1) corresponds to a predetermined distance between the X-ray source 105 and the X-ray detector 30, a user may confirm that the X-ray source 105 is placed in an input distance, via the input unit 162

As illustrated in FIG. 5, a user may confirm whether a distance between the X-ray source 105 and the X-ray detector 30 corresponds to a reference distance or not, based on distance information that is input via the input unit 162, and a position in which a light irradiated from the reference light emitter 1000 and a light irradiated from the second auxiliary light emitter 1020 are overlapped, and thus the user may adjust the position of the X-ray source 105.

Figure 6:
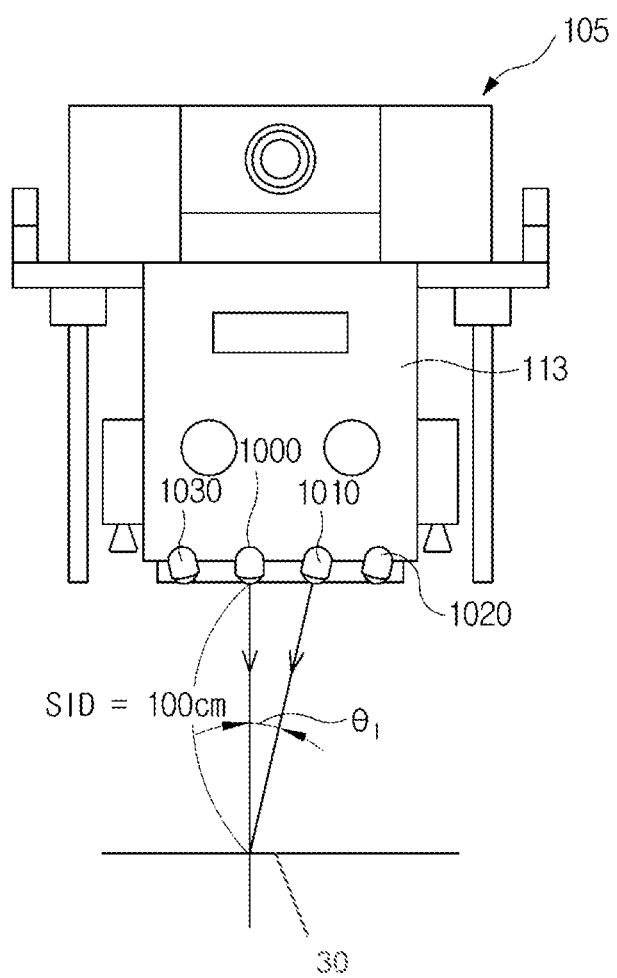
FIGS. 6 to 8 illustrate front views of irradiating a light from a reference light emitter and an auxiliary light emitter based on distance information in accordance with an embodiment of the present disclosure.
Figure 7:
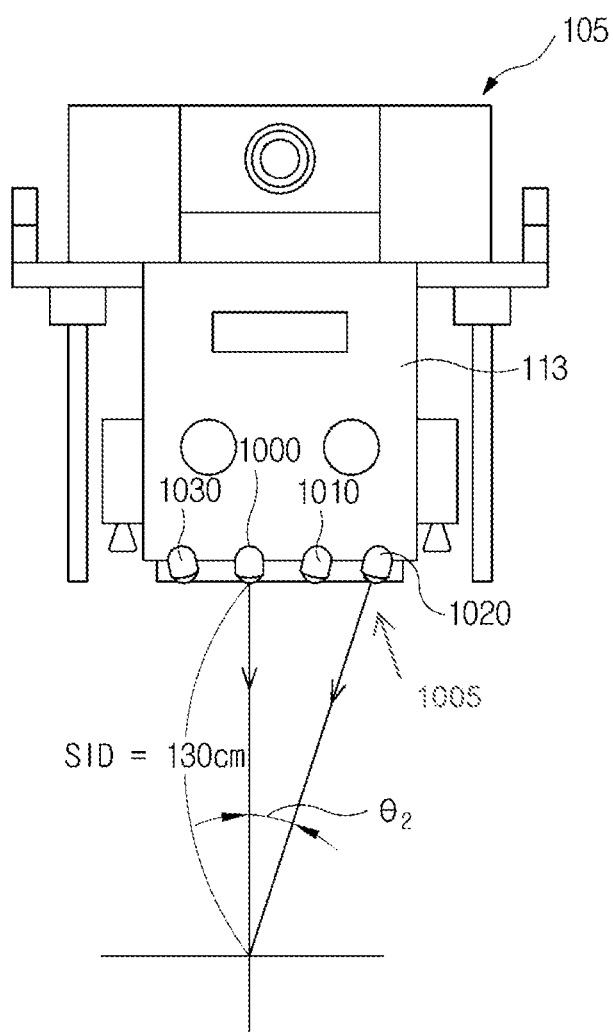
Figure 8:
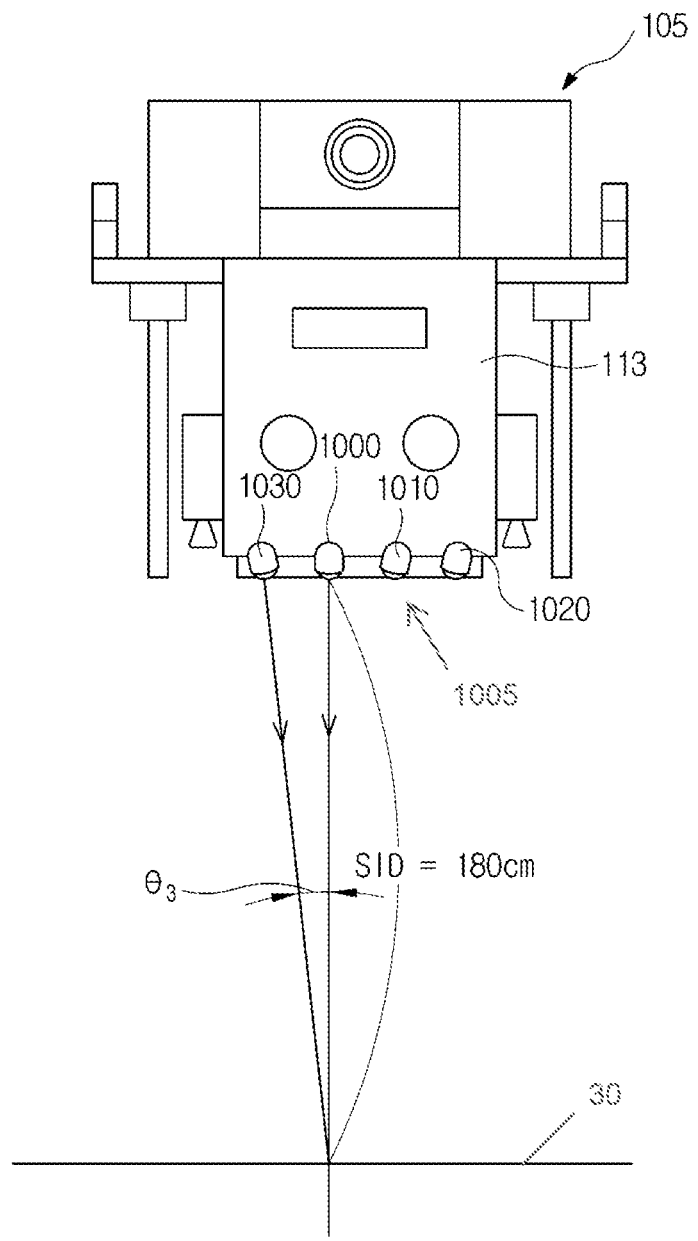

FIGS. 6 to 8 illustrate front views of irradiating a light from a reference light emitter 1000 and an auxiliary light emitter 1005 based on distance information in accordance with an embodiment of the present disclosure.

As mentioned above, in a case of performing an X-ray imaging of an object, a distance between the X-ray source 105 and the X-ray detector 30 may be defined as "source-image distance (SID)" wherein the SID value may vary according to the type or a target part of an object of X-ray imaging.

A reference unit of the SID may typically include 100 cm, 130 cm, and 180 cm, and it may represent that the X-ray detector 30 is needed to be placed in a position apart from the X-ray source 105 by 100 cm, 130 cm, and 180 cm according to the type or a target part of X-ray imaging object.

In FIGS. 6 to 8, SID may be defined as a distance between the reference light emitter 1000 and the X-ray detector 30.

FIG. 6 illustrates a case in which a SID value is 100 cm as an example. Prior to performing an X-ray imaging, a user may need to adjust a distance between the X-ray source 105 and the X-ray detector 30 as 100 cm to perform the X-ray imaging, and thus the user may input distance information between the X-ray source 105 and the X-ray detector 30, via the input unit 162.

When a SID is 100 cm, the distance between the X-ray source 105 and the X-ray detector 30 may be needed to be set to 100 cm to perform the X-ray imaging. When a user inputs distance information including that a SID is 100 cm, via the input unit 162, the controller 150 may turn on the first auxiliary light emitter 1010 and the reference light emitter 1000 to adjust a distance when a SID is 100 cm, based on a corresponding relation between distance information stored in the storage 170 and the first auxiliary light emitter 1010.

The first auxiliary light emitter 1010 may be installed to have an angle of θ1 with the reference light emitter 1000 with respect to the Y axis, and thus a light irradiated from the reference light emitter 1000 and a light irradiated from the first auxiliary light emitter 1010 may be overlapped in a position apart from the reference light emitter 1000 by 100 cm while having an angle of θ1.

Therefore, a user may confirm the overlapped line (L1) that is placed in a position apart from the reference light emitter 1000 by 100 cm, and then the user may adjust the height of the X-ray source 105 so that the overlapped line (L1) is placed on the X-ray detector 30.

FIG. 7 illustrates a case in which a SID value is 130 cm as an example. Prior to performing an X-ray imaging, a user may need to adjust a distance between the X-ray source 105 and the X-ray detector 30 as 130 cm to perform the X-ray imaging, and thus the user may input distance information between the X-ray source 105 and the X-ray detector 30, via the input unit 162.

When a SID is 130 cm, the distance between the X-ray source 105 and the X-ray detector 30 may be needed to be set to 130 cm to perform the X-ray imaging. When a user inputs distance information including that a SID is 130 cm, via the input unit 162, the controller 150 may turn on the second auxiliary light emitter 1020 and the reference light emitter 1000 to adjust a distance when a SID is 130 cm, based on a corresponding relation between distance information stored in the storage 170 and the second auxiliary light emitter 1020.

The second auxiliary light emitter 1020 may be installed to have an angle of θ2 with the reference light emitter 1000 with respect to the Y axis, and thus a light irradiated from the reference light emitter 1000 and a light irradiated from the second auxiliary light emitter 1020 may be overlapped in a position apart from the reference light emitter 1000 by 130 cm while having an angle of θ2.

Therefore, a user may confirm an overlapped line (L1) that is placed in a position apart from the reference light emitter 1000 by 130 cm, and then the user may adjust the height of the X-ray source 105 so that the overlapped line (L1) is placed on the X-ray detector 30.

FIG. 8 illustrates a case in which a SID value is 180 cm as an example. Prior to performing an X-ray imaging, a user may need to adjust a distance between the X-ray source 105 and the X-ray detector 30 as 180 cm to perform the X-ray imaging, and thus the user may input distance information between the X-ray source 105 and the X-ray detector 30, via the input unit 162.

When a SID is 180 cm, the distance between the X-ray source 105 and the X-ray detector 30 may be needed to be set to 180 cm to perform the X-ray imaging. When a user inputs distance information including that a SID is 180 cm, via the input unit 162, the controller 150 may turn on the third auxiliary light emitter 1030 and the reference light emitter 1000 to adjust a distance when a SID is 180 cm, based on a corresponding relation between distance information stored in the storage 170 and the third auxiliary light emitter 1030.

The third auxiliary light emitter 1030 may be installed to have an angle of θ3 with the reference light emitter 1000 with respect to the Y axis, and thus a light irradiated from the reference light emitter 1000 and a light irradiated from the third auxiliary light emitter 1030 may be overlapped in a position apart from the reference light emitter 1000 by 180 cm while having an angle of θ3.

Therefore, a user may confirm an overlapped line (L1) that is placed in a position apart from the reference light emitter 1000 by 180 cm, and then the user may adjust the height of the X-ray source 105 so that the overlapped line (L1) is placed on the X-ray detector 30.

Figure 9:
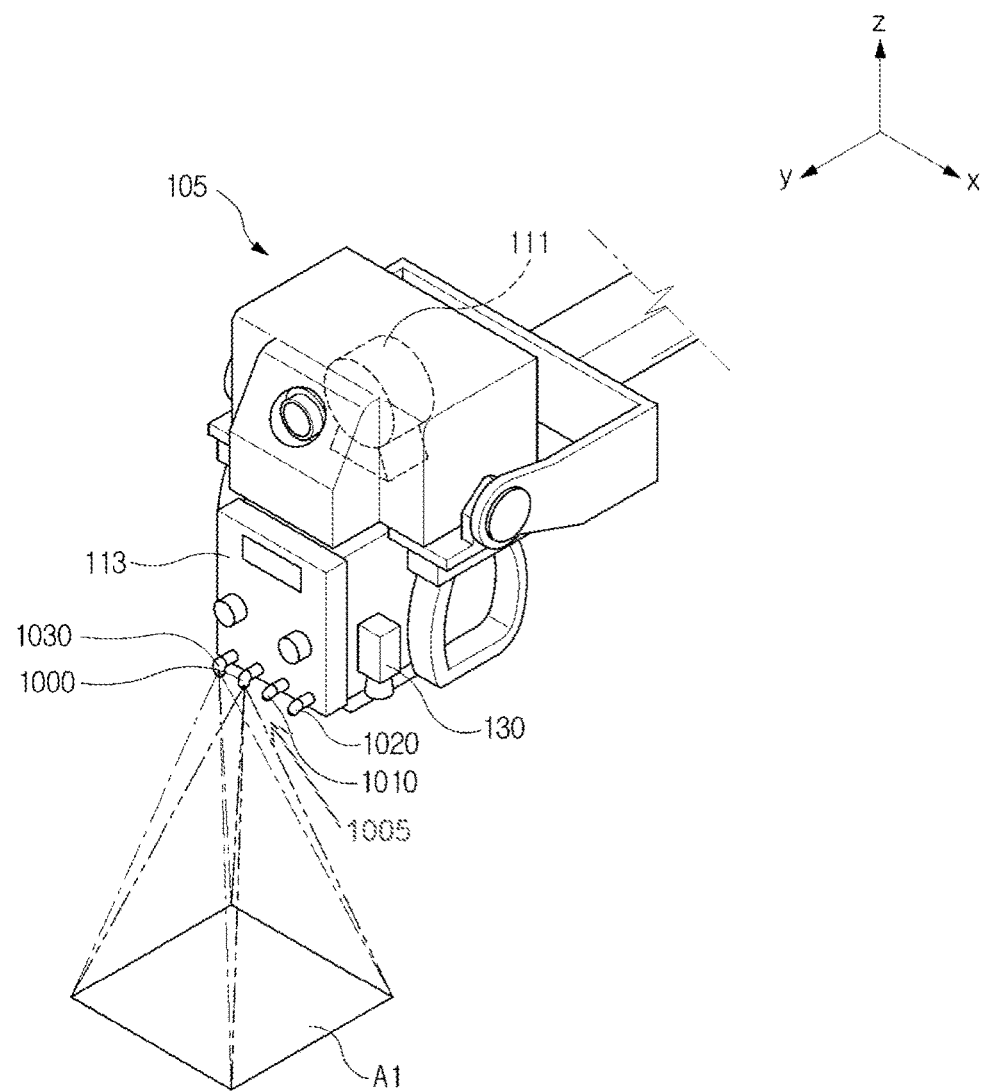
FIG. 9 illustrates a schematic view of a case in which a light irradiated from a reference light emitter and an auxiliary light emitter are overlapped to have a square shape in a predetermined distance in accordance with another embodiment of the present disclosure.
Figure 10:
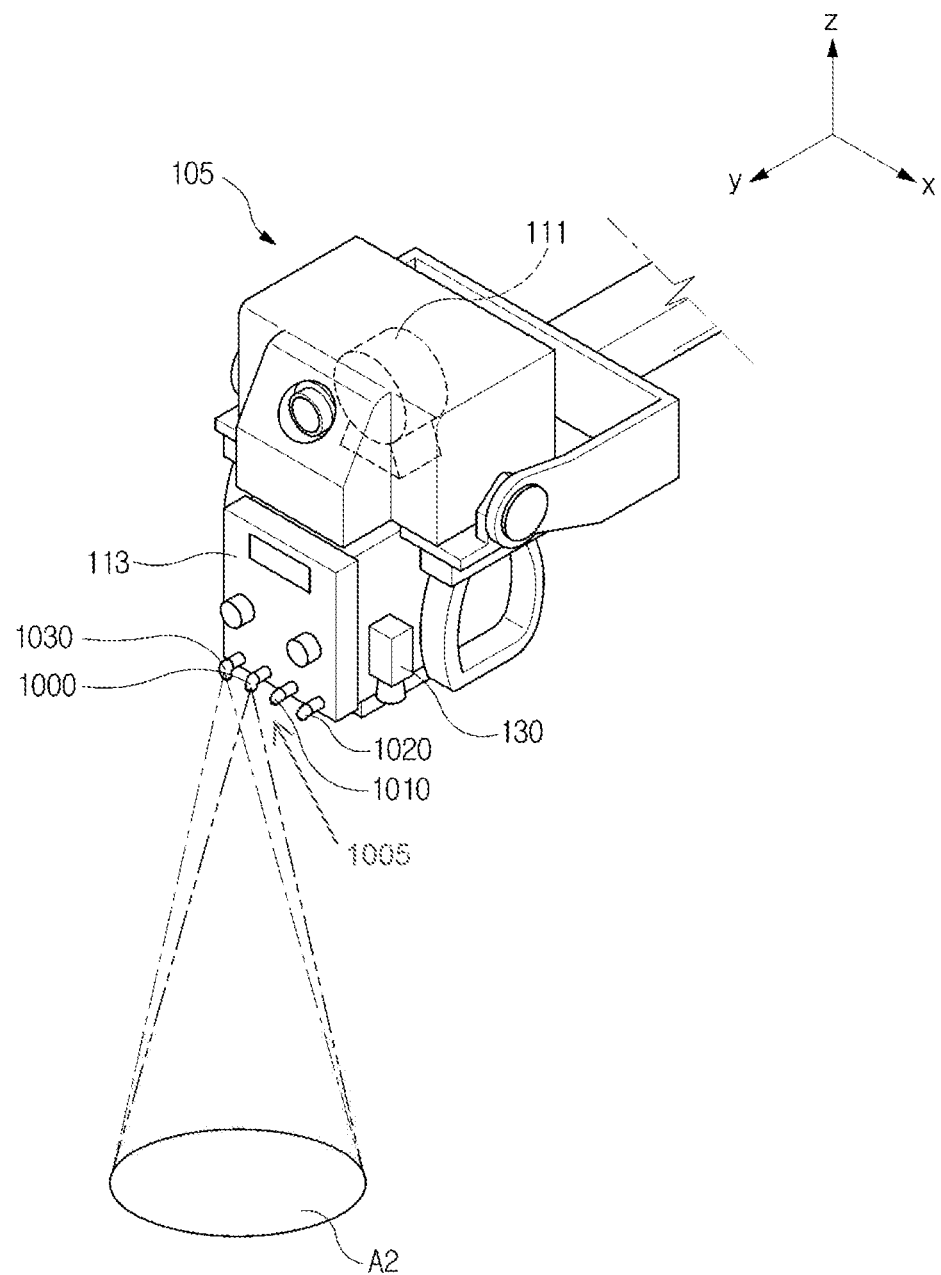
FIG. 10 illustrates a schematic view of a case in which a light irradiated from a reference light emitter and an auxiliary light emitter are overlapped to have a circular shape in a predetermined distance in accordance with another embodiment of the present disclosure.

FIG. 9 illustrates a schematic view in which a light irradiated from a reference light emitter 1000 and an auxiliary light emitter are overlapped to have a square shape (A1) in a predetermined distance in accordance with another embodiment of the present disclosure, and FIG. 10 illustrates a schematic view in which a light irradiated from a reference light emitter 1000 and an auxiliary light emitter are overlapped to have a circular shape (A2) in a predetermined distance in accordance with another embodiment of the present disclosure.

As mentioned above, the reference light emitter 1000 and the third auxiliary light emitter 1030 may irradiate a light to a direction in which the X-ray detector 30 is placed. FIG. 5 illustrates that the reference light emitter 1000 and the third auxiliary light emitter 1030 irradiate a flat light to a direction in which the X-ray detector 30 is placed, but alternatively, FIG. 9 illustrates that the reference light emitter 1000 and the third auxiliary light emitter 1030 irradiate a light having quadrangular pyramid shape.

As illustrated in FIG. 9, a light having quadrangular pyramid shape may be irradiated from the reference light emitter 1000 and the third auxiliary light emitter 1030. Since the light having quadrangular pyramid shape has a cross-sectional surface having a square shape, two lights may be overlapped to have a square shape in comparison with the flat light.

That is, a light irradiated from the reference light emitter 1000 and the third auxiliary light emitter 1030 may be overlapped in a position in which a SID is 180 cm, and an overlapped light may have a square shape (A1), as illustrated in FIG. 9.

A user may confirm a position of the square shape (A1) in which a light irradiated from the reference light emitter 1000 and a light irradiated from the third auxiliary light emitter 1030 are overlapped, and then adjust the position of the X-ray source 105 so that a distance between the X-ray source 105 and the X-ray detector 30 (FIG. 2A) becomes 180 cm.

FIG. 10 illustrates that the reference light emitter 1000 and the third auxiliary light emitter 1030 irradiate a light having a conical shape.

As illustrated in FIG. 10, a light having a conical shape may be irradiated from the reference light emitter 1000 and the third auxiliary light emitter 1030. Since the light having a conical shape has a cross-sectional surface having a circular shape, two lights may be overlapped to have a circular shape in comparison with the flat light.

That is, a light irradiated from the reference light emitter 1000 and the third auxiliary light emitter 1030 may be overlapped in a position in which a SID is 180 cm, and an overlapped light may have a circular shape (A2), as illustrated in FIG. 10.

A user may confirm a position of the circular shape (A2) in which a light irradiated from the reference light emitter 1000 and a light irradiated from the third auxiliary light emitter 1030 are overlapped, and then adjust the position of the X-ray source 105 so that a distance between the X-ray source 105 and the X-ray detector 30 (FIG. 2A) becomes 180 cm.

Figure 11:
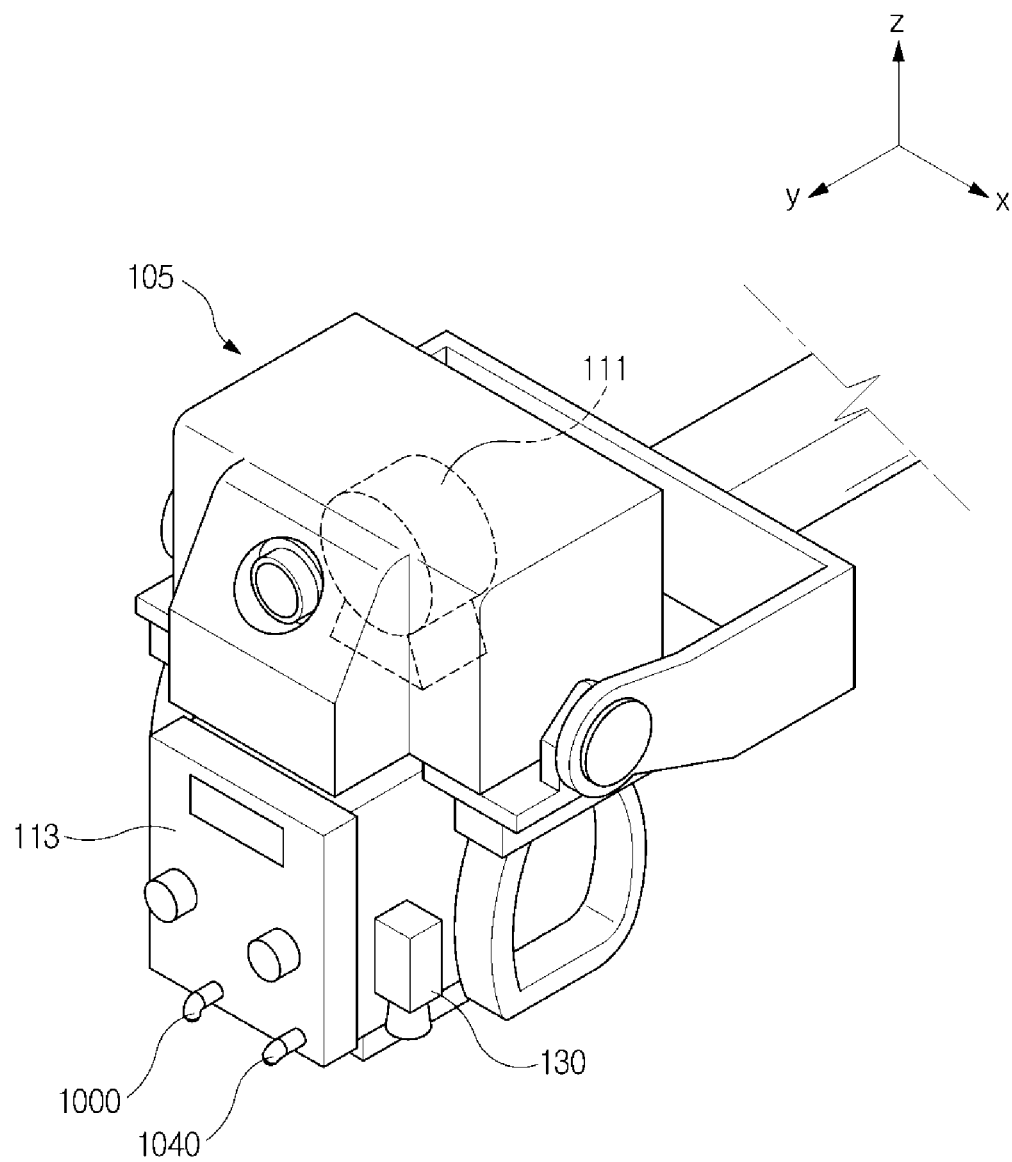
FIG. 11 illustrates a schematic view of an angle adjustment light emitter provided in an X-ray source in accordance with an embodiment of the present disclosure.

FIG. 11 illustrates a schematic view of an angle adjustment light emitter 1040 provided in an X-ray source 105 in accordance with an embodiment of the present disclosure.

Referring to FIG. 11, the X-ray source 105 of the X-ray imaging apparatus 100 may include the angle adjustment light emitter 1040, and although not shown in the FIG. 11, the angle adjustment light emitter 1040 may include the first driving motor 1041 (FIG. 4).

For convenience of description, FIG. 11 illustrates only the reference light emitter 1000 and the angle adjustment light emitter 1040, but the first auxiliary light emitter 1010, the second auxiliary light emitter 1020, and the third auxiliary light emitter 1030 may be provided in the X-ray source 105 as well as the angle adjustment light emitter 1040.

There may be no limitation in a position in which the angle adjustment light emitter 1040 is installed, as long as being adjacent to the X-ray source 105 and configured to irradiate a light to a direction of the X-ray detector 30. As illustrated in FIG. 11, the angle adjustment light emitter 1040 may be installed apart from the reference light emitter 1000 by a predetermined distance, and the predetermined distance may be determined in consideration with whether a light irradiated from the reference light emitter 1000 and a light irradiated from the angle adjustment light emitter 1040 are overlapped.

The angle adjustment light emitter 1040 may include the first driving motor 1041 (FIG. 4), and the first driving motor 1041 may rotate the angle adjustment light emitter 1040 under a control of the controller 150. Accordingly, an angle of a light irradiated from the angle adjustment light emitter 1040 may be changed.

That is, when receiving an input of SID information between the X-ray source 105 and the X-ray detector 30 from a user via the input unit 162, the controller 150 may control the first driving motor 1041 (FIG. 4) and the angle adjustment light emitter 1040 may be rotated to allow the irradiation angle of the light to be changed, based on SID information stored in the storage 170 and an irradiation angle of a light of the angle adjustment light emitter 1040 corresponding to the SID information.

Figure 12:
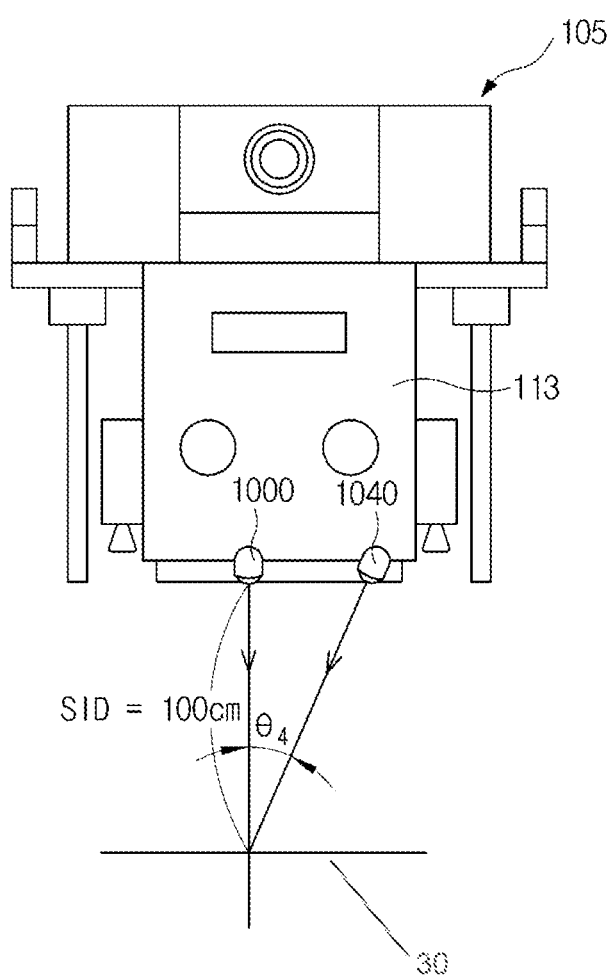
FIGS. 12 to 14 illustrate front views of a case in which a light is irradiated from a reference light emitter and an auxiliary light emitter based on distance information in accordance with an embodiment of the present disclosure.
Figure 13:
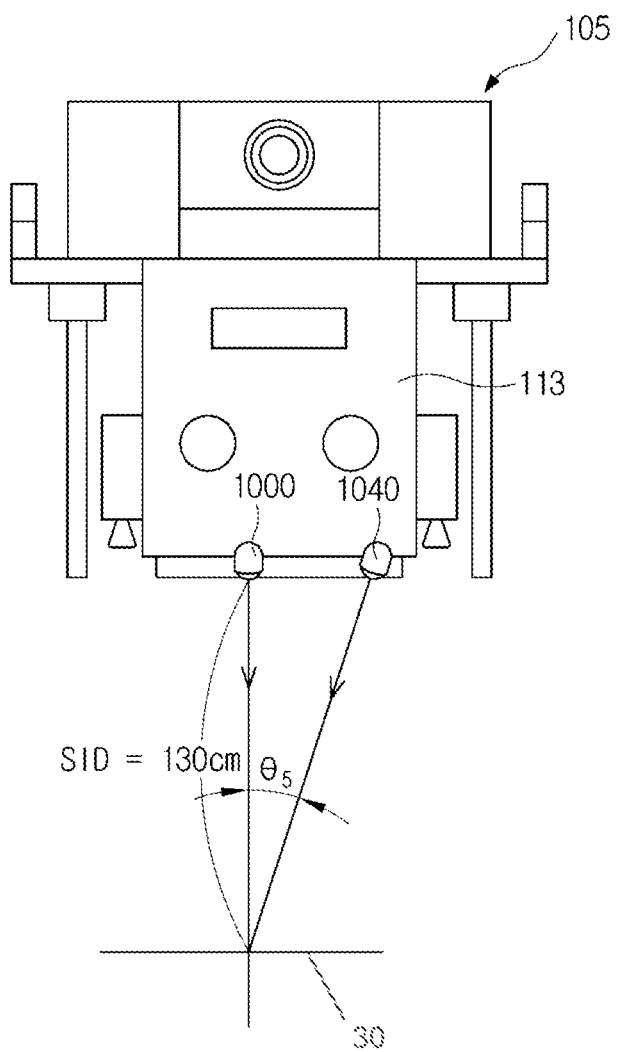
Figure 14:
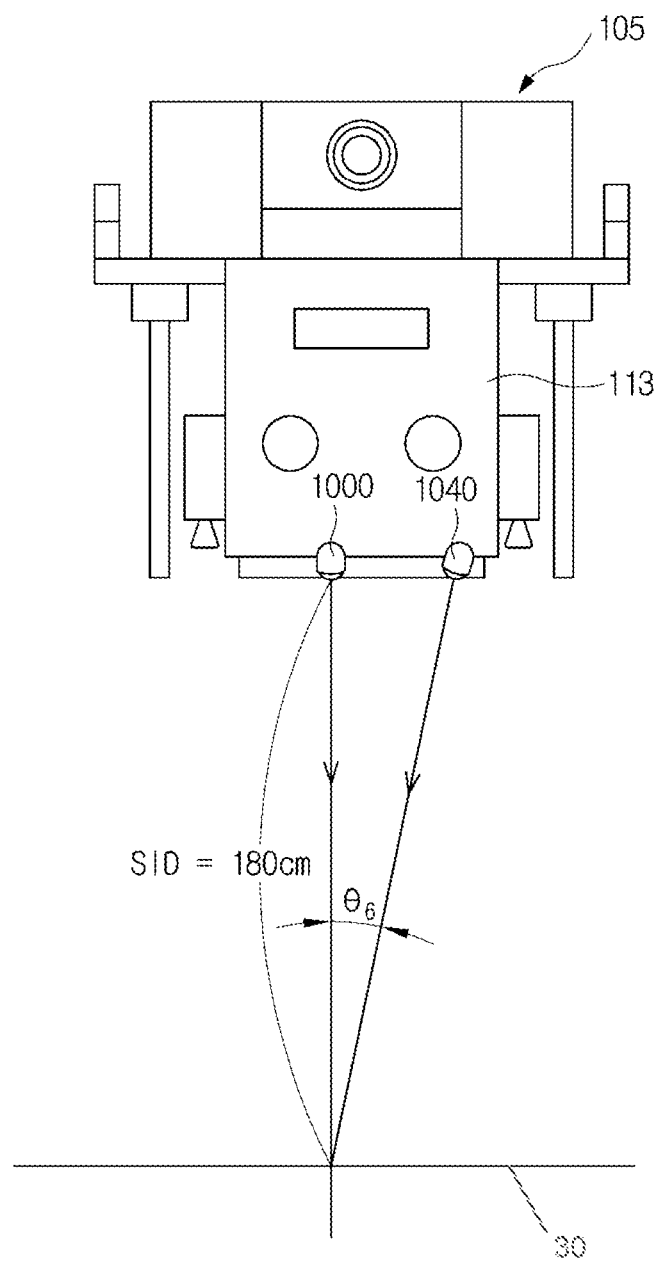

FIGS. 12 to 14 illustrate front views in which a light is irradiated from a reference light emitter 1000 and an auxiliary light emitter 1005 based on distance information in accordance with an embodiment of the present disclosure.

For convenience of description, FIGS. 12 to 14 illustrate only the reference light emitter 1000 and the angle adjustment light emitter 1040, but the first auxiliary light emitter 1010, the second auxiliary light emitter 1020, and the third auxiliary light emitter 1030 may be provided in the X-ray source 105 as well as the angle adjustment light emitter 1040.

FIG. 12 illustrates a case in which a SID value is 100 cm as an example. Prior to performing an X-ray imaging, a user may need to adjust a distance between the X-ray source 105 and the X-ray detector 30 as 100 cm to perform the X-ray imaging, and thus the user may input distance information between the X-ray source 105 and the X-ray detector 30, via the input unit 162.

When a SID is 100 cm, the distance between the X-ray source 105 and the X-ray detector 30 may be needed to be set to 100 cm to perform the X-ray imaging. When a user inputs distance information including that a SID is 100 cm, via the input unit 162, the controller 150 may control the first driving motor 1041 based on SID information including that a SID is 100 cm stored in the storage 170 and an irradiation angle of a light of the angle adjustment light emitter 1040 corresponding to the SID information, and accordingly, the angle adjustment light emitter 1040 may be rotated to be set to an irradiation angle of θ4 corresponding to a fact that SID is 100 cm. In addition, the controller 150 may turn on the reference light emitter 1000 and the angle adjustment light emitter 1040.

That is, the angle adjustment light emitter 1040 may be rotated to have an angle of θ4 with the reference light emitter 1000 with respect to the Y axis, and thus a light irradiated from the reference light emitter 1000 and a light irradiated from the angle adjustment light emitter 1040 may be overlapped in a position apart from the reference light emitter 1000 by 100 cm to have an angle of θ4.

Therefore, a user may confirm the overlapped line (L1) that is placed in a position apart from the reference light emitter 1000 by 100 cm, and then the user may adjust the height of the X-ray source 105 so that the overlapped line (L1) is placed on the X-ray detector 30.

FIG. 13 illustrates a case in which a SID value is 130 cm as an example. When a SID is 130 cm, the distance between the X-ray source 105 and the X-ray detector 30 may be needed to be set to 130 cm to perform the X-ray imaging. When a user inputs distance information including that a SID is 130 cm, via the input unit 162, the controller 150 may control the first driving motor 1041 based on SID information including that a SID is 130 cm stored in the storage 170 and an irradiation angle of a light of the angle adjustment light emitter 1040 corresponding to the SID information, and accordingly, the angle adjustment light emitter 1040 may be rotated to be set to an irradiation angle of $\theta_5$ corresponding to a fact that SID is 130 cm. In addition, the controller 150 may turn on the reference light emitter 1000 and the angle adjustment light emitter 1040.

That is, the angle adjustment light emitter 1040 may be rotated to have an angle of $\theta_5$ with the reference light emitter 1000 with respect to the Y axis, and thus a light irradiated from the reference light emitter 1000 and a light irradiated from the angle adjustment light emitter 1040 may be overlapped in a position apart from the reference light emitter 1000 by 130 cm to have an angle of $\theta_5$.

Therefore, a user may confirm the overlapped line (L1) that is placed in a position apart from the reference light emitter 1000 by 130 cm, and then the user may adjust the height of the X-ray source 105 so that the overlapped line (L1) is placed on the X-ray detector 30.

FIG. 14 illustrates a case in which a SID value is 180 cm as an example. When a SID is 180 cm, the distance between the X-ray source 105 and the X-ray detector 30 may be needed to be set to 180 cm to perform the X-ray imaging. When a user inputs distance information including that a SID is 180 cm, via the input unit 162, the controller 150 may control the first driving motor 1041 based on SID information including that a SID is 180 cm stored in the storage 170 and an irradiation angle of a light of the angle adjustment light emitter 1040 corresponding to the SID information, and accordingly, the angle adjustment light emitter 1040 may be rotated to be set to an irradiation angle of $\theta_6$ corresponding to a fact that SID is 180 cm. In addition, the controller 150 may turn on the reference light emitter 1000 and the angle adjustment light emitter 1040.

That is, the angle adjustment light emitter 1040 may be rotated to have an angle of $\theta_6$ with the reference light emitter 1000 with respect to the Y axis, and thus a light irradiated from the reference light emitter 1000 and a light irradiated from the angle adjustment light emitter 1040 may be overlapped in a position apart from the reference light emitter 1000 by 180 cm to have an angle of $\theta_6$.

Therefore, a user may confirm the overlapped line (L1) that is placed in a position apart from the reference light emitter 1000 by 180 cm, and then the user may adjust the height of the X-ray source 105 so that the overlapped line (L1) is placed on the X-ray detector 30.

Figure 15:
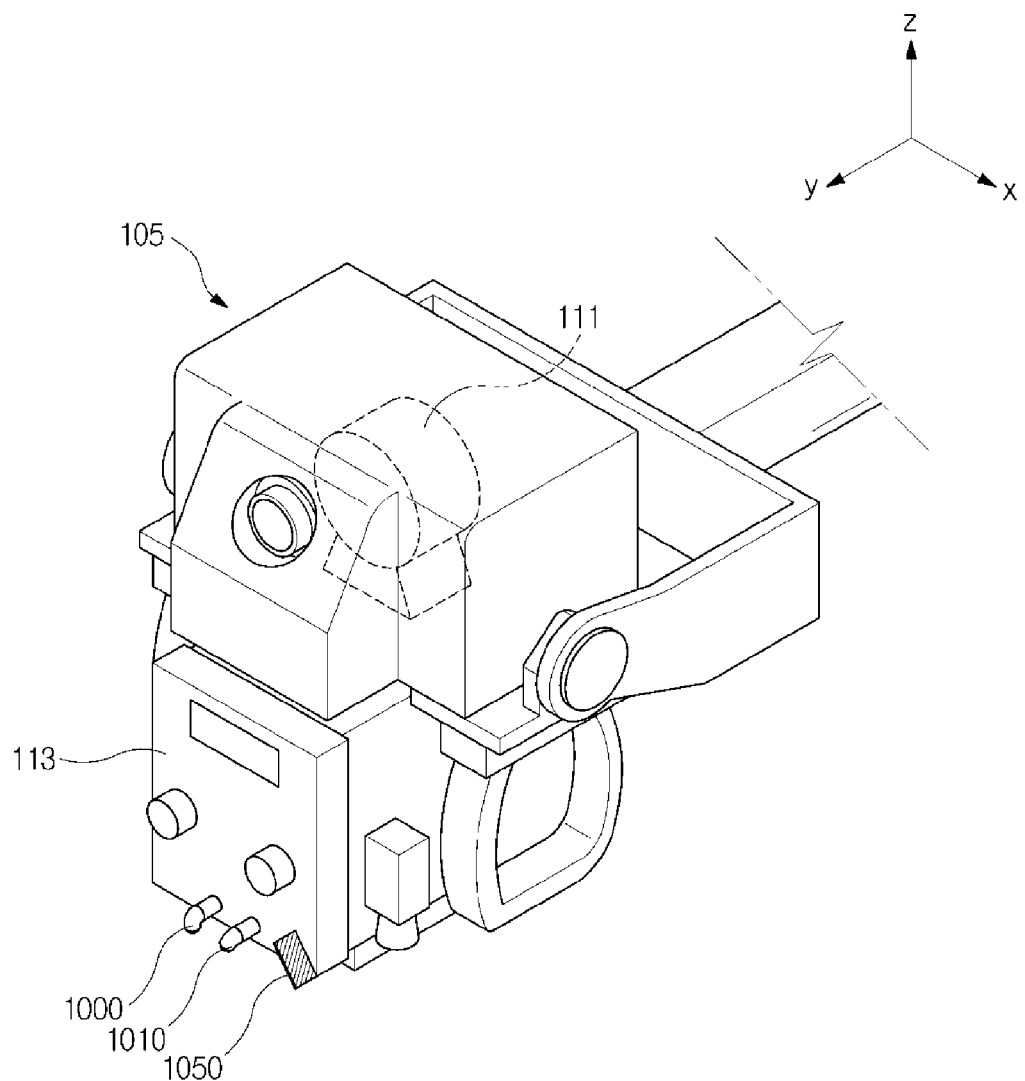
FIG. 15 illustrates a schematic view of a light reflector provided in an X-ray source in accordance with an embodiment of the present disclosure.

FIG. 15 illustrates a schematic view of a light reflector provided in an X-ray source in accordance with an embodiment of the present disclosure.

Referring to FIG. 15, the X-ray source 105 of the X-ray imaging apparatus 100 may include the light reflector 1050, and although not shown in the FIG. 15, the light reflector 1050 may include the second driving motor 1052 (FIG. 4).

For convenience of description, FIG. 15 illustrates only the reference light emitter 1000, the first auxiliary light emitter 1010, and the light reflector 1050, but as well as the reference light emitter 1000, the first auxiliary light emitter 1010, and the light reflector 1050, the second auxiliary light emitter 1020 and the third auxiliary light emitter 1030 may be provided in the X-ray source 105.

There may be no limitation in a position in which the light reflector 1050 is installed, as long as being adjacent to the X-ray source 105 and configured to irradiate a light irradiated from the first auxiliary light emitter 1010 to a direction of the X-ray detector 30.

As illustrated in FIG. 15, the light reflector 1050 may be installed apart from the reference light emitter 1000 and the first auxiliary light emitter 1010 by a predetermined distance, and the light reflector 1050 may reflect a light irradiated from the first auxiliary light emitter 1010 by including the second driving motor 1052. In this case, the predetermined distance may be determined in consideration with whether a light irradiated from the reference light emitter 1000 and a light reflected by the light reflector 1050 are overlapped.

Unlike FIG. 3, the first auxiliary light emitter 1010 may be provided to allow a light source thereof to face the light reflector 1050 so as to irradiate a light to the light reflector 1050. FIG. 15 illustrates that the light reflector 1050 reflects a light irradiated from the first auxiliary light emitter 1010 to a direction of the X-ray detector 30, as an example, but the light reflector 1050 may reflect a light irradiated from the second auxiliary light emitter 1020 or the third auxiliary light emitter 1030 to a direction of the X-ray detector 30. In this case, as the same as the first auxiliary light emitter 1010, the second auxiliary light emitter 1020 or the third auxiliary light emitter 1030 may be provided to allow a light source thereof to face the light reflector 1050 so as to irradiate a light to the light reflector 1050.

The light reflector 1050 may include the second driving motor 1052 (FIG. 4), and the second driving motor 1052 may rotate the light reflector 1050 under a control of the controller 150. Accordingly, a reflection angle of a light irradiated from the first auxiliary light emitter 1010 may be changed.

That is, when receiving an input of SID information between the X-ray source 105 and the X-ray detector 30 from a user via the input unit 162, the controller 150 may control the second driving motor 1052 (FIG. 4) and rotate the light reflector 1050 so that the reflection angle of the light is changed, based on SID information stored in the storage 170 and an irradiation angle of a light of the light reflector 1050 corresponding to the SID information.

Figure 16:
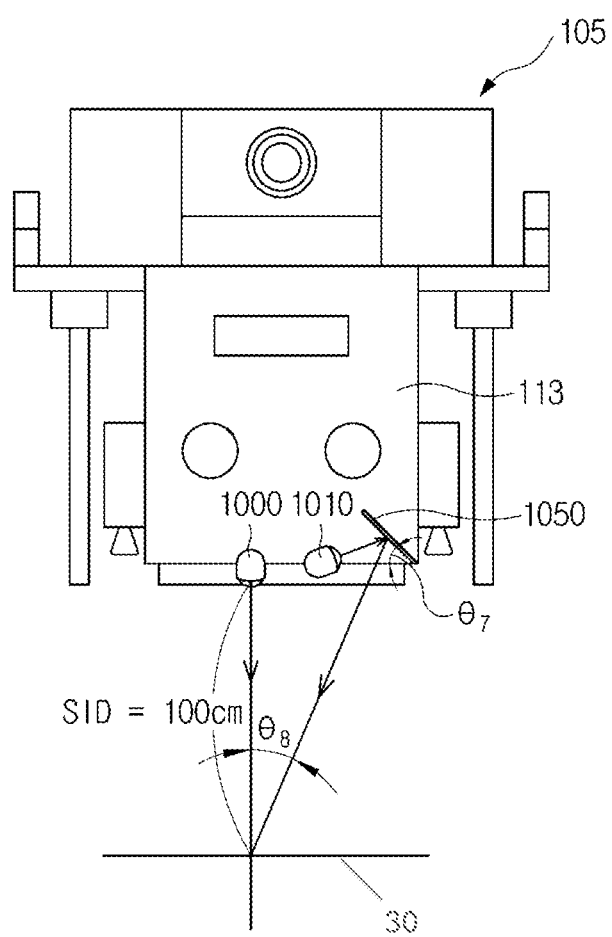
FIGS. 16 to 18 illustrate front views of a case in which a light is irradiated from a reference light emitter and a light irradiated from an auxiliary light emitter is reflected by a light reflector based on distance information in accordance with an embodiment of the present disclosure.
Figure 17:
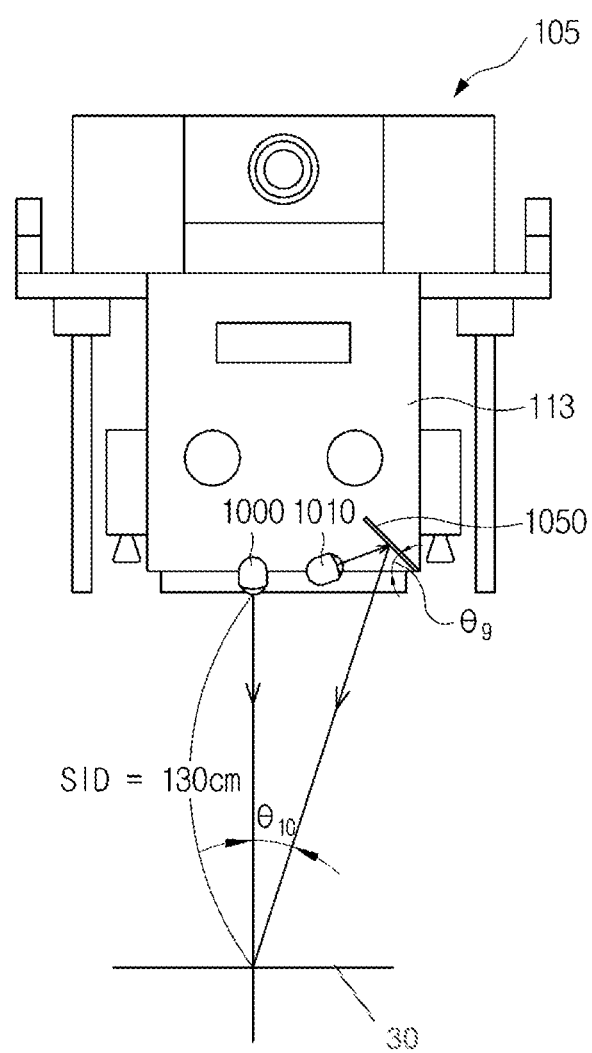
Figure 18:
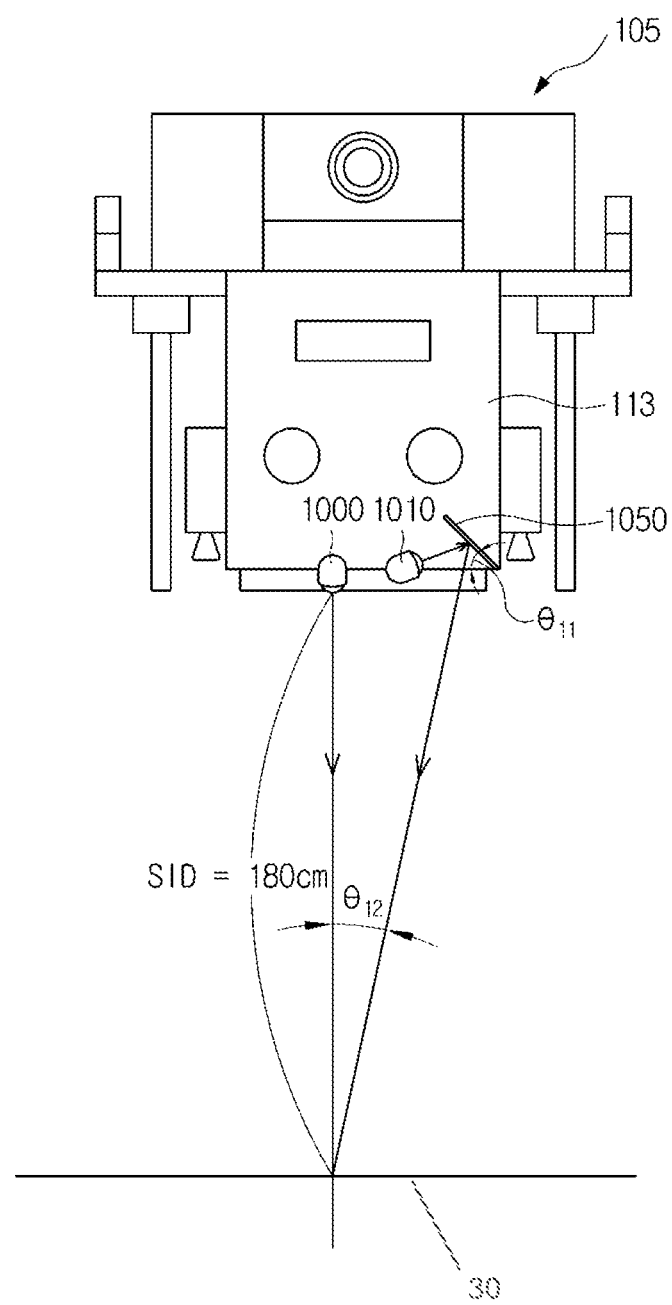

FIGS. 16 to 18 illustrate front views in which a light is irradiated from a reference light emitter and a light irradiated from an auxiliary light emitter is reflected by a light reflector based on distance information in accordance with an embodiment of the present disclosure.

For convenience of description, FIGS. 16 to 18 illustrate only the reference light emitter 1000, the first auxiliary light emitter 1010, and the light reflector 1050, but as well as the reference light emitter 1000, the first auxiliary light emitter 1010, and the light reflector 1050, the second auxiliary light emitter 1020 and the third auxiliary light emitter 1030 may be provided in the X-ray source 105.

FIG. 16 illustrates a case in which a SID value is 100 cm as an example. Prior to performing an X-ray imaging, a user may need to adjust a distance between the X-ray source 105 and the X-ray detector 30 as 100 cm to perform the X-ray imaging, and thus the user may input distance information between the X-ray source 105 and the X-ray detector 30, via the input unit 162.

When a SID is 100 cm, the distance between the X-ray source 105 and the X-ray detector 30 may be needed to be set to 100 cm to perform the X-ray imaging. When a user inputs distance information including that a SID is 100 cm, via the input unit 162, the controller 150 may control the second driving motor 1052 based on SID information including that a SID is 100 cm stored in the storage 170 and a reflection angle of a light of the light reflector 1050 corresponding to the SID information, and accordingly, the light reflector 1050 may be rotated to be set to a reflection angle of $\theta 8$ corresponding to a fact that SID is 100 cm. In addition, the controller 150 may turn on the reference light emitter 1000 and the first auxiliary light emitter 1010.

For convenience of description, FIG. 16 illustrates that a light is irradiated from the first auxiliary light emitter 1010, but a light may be irradiated from the second auxiliary light emitter 1020 or the third auxiliary light emitter 1030 instead of the first auxiliary light emitter 1010. However, any one of the first auxiliary light emitter 1010, the second auxiliary light emitter 1020, and the third auxiliary light emitter 1030 may be needed to be installed to irradiate a light to the light reflector 1050.

That is, the light reflector 1050 may be rotated to have an angle of $\theta_7$ with respect to the X axis, and thus a light irradiated from the reference light emitter 1000 and a light, which is irradiated from the first auxiliary light emitter 1010 and then reflected by the light reflector 1050, may be overlapped in a position apart from the reference light emitter 1000 by 100 cm to have an angle of $\theta_8$.

Therefore, a user may confirm the overlapped line (L1) that is placed in a position apart from the reference light emitter 1000 by 100 cm, and then the user may adjust the height of the X-ray source 105 so that the overlapped line (L1) is placed on the X-ray detector 30.

FIG. 17 illustrates a case in which a SID value is 130 cm as an example.

When a SID is 130 cm, the distance between the X-ray source 105 and the X-ray detector 30 may be needed to be set to 130 cm to perform the X-ray imaging. When a user inputs distance information including that a SID is 130 cm, via the input unit 162, the controller 150 may control the second driving motor 1052 based on SID information including that a SID is 130 cm stored in the storage 170 and a reflection angle of a light of the light reflector 1050 corresponding to the SID information, and accordingly, the light reflector 1050 may be rotated to be set to a reflection angle of $\theta 10$ corresponding to a fact that SID is 130 cm. In addition, the controller 150 may turn on the reference light emitter 1000 and the first auxiliary light emitter 1010.

That is, the light reflector 1050 may be rotated to have an angle of $\theta_9$ with respect to the X axis, and thus a light irradiated from the reference light emitter 1000 and a light, which is irradiated from the first auxiliary light emitter 1010 and then reflected by the light reflector 1050, may be overlapped in a position apart from the reference light emitter 1000 by 130 cm to have an angle of $\theta_{10}$.

Therefore, a user may confirm the overlapped line (L1) that is placed in a position apart from the reference light emitter 1000 by 130 cm, and then the user may adjust the height of the X-ray source 105 so that the overlapped line (L1) is placed on the X-ray detector 30.

FIG. 18 illustrates a case in which a SID value is 180 cm as an example.

When a SID is set to 180 cm, the distance between the X-ray source 105 and the X-ray detector 30 may be needed to be set to 180 cm to perform the X-ray imaging. When a user inputs distance information including that a SID is 180 cm, via the input unit 162, the controller 150 may control the second driving motor 1052 based on SID information including that a SID is 180 cm stored in the storage 170 and a reflection angle of a light of the light reflector 1050 corresponding to the SID information, and accordingly, the light reflector 1050 may be rotated to be set to a reflection angle of $\theta_{12}$ corresponding to a fact that SID is 180 cm. In addition, the controller 150 may turn on the reference light emitter 1000 and the first auxiliary light emitter 1010.

That is, the light reflector 1050 may be rotated to have an angle of $\theta_{11}$ with respect to the X axis, and thus a light irradiated from the reference light emitter 1000 and a light, which is irradiated from the first auxiliary light emitter 1010 and then reflected by the light reflector 1050, may be overlapped in a position apart from the reference light emitter 1000 by 180 cm to have an angle of $\theta_{12}$.

Therefore, a user may confirm the overlapped line (L1) that is placed in a position apart from the reference light emitter 1000 by 180 cm, and then the user may adjust the height of the X-ray source 105 so that the overlapped line (L1) is placed on the X-ray detector 30.

Figure 19:
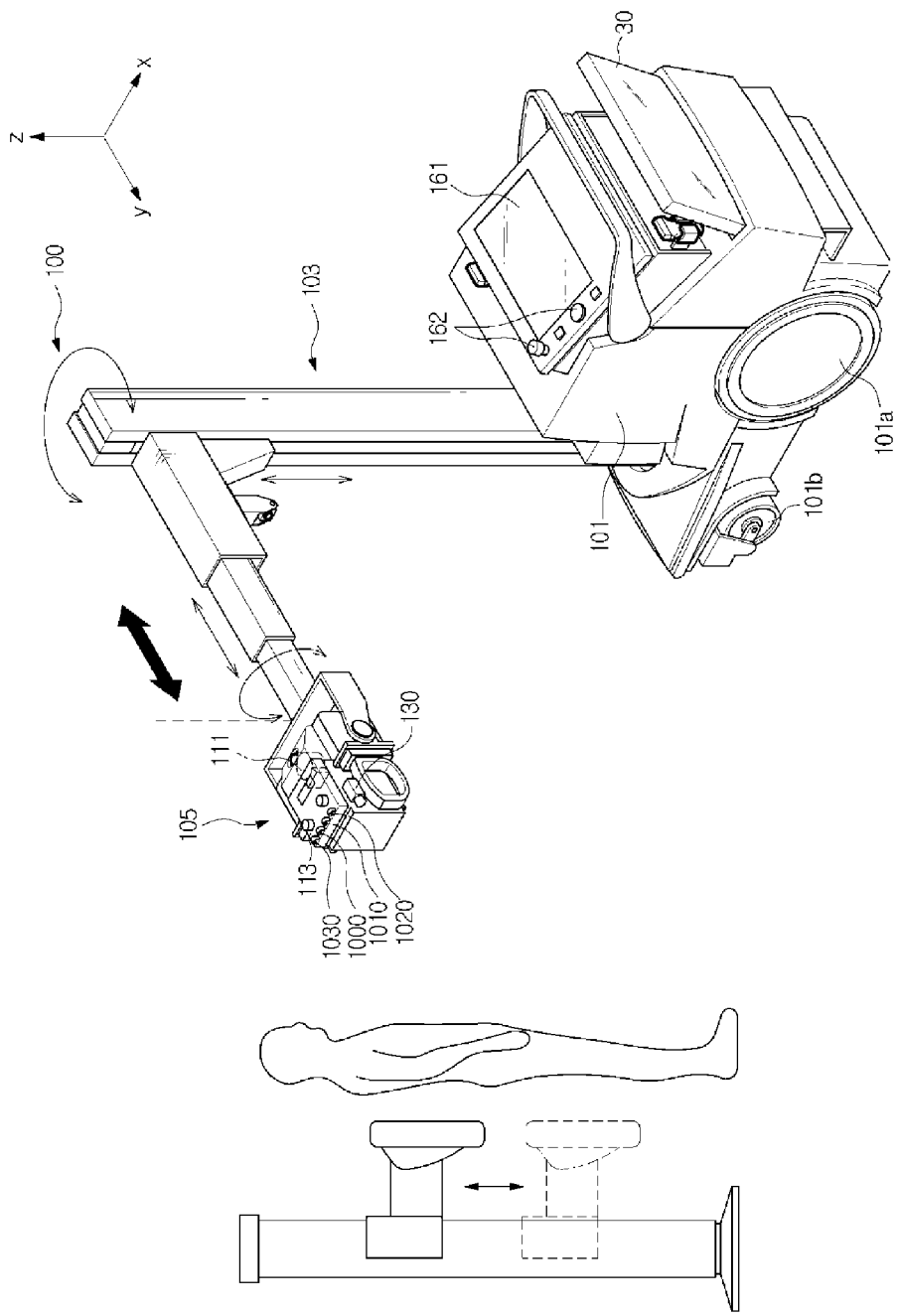
FIG. 19 illustrates a schematic view of imaging an object by rotating an X-ray source in accordance with another embodiment of the present disclosure.
Figure 20:
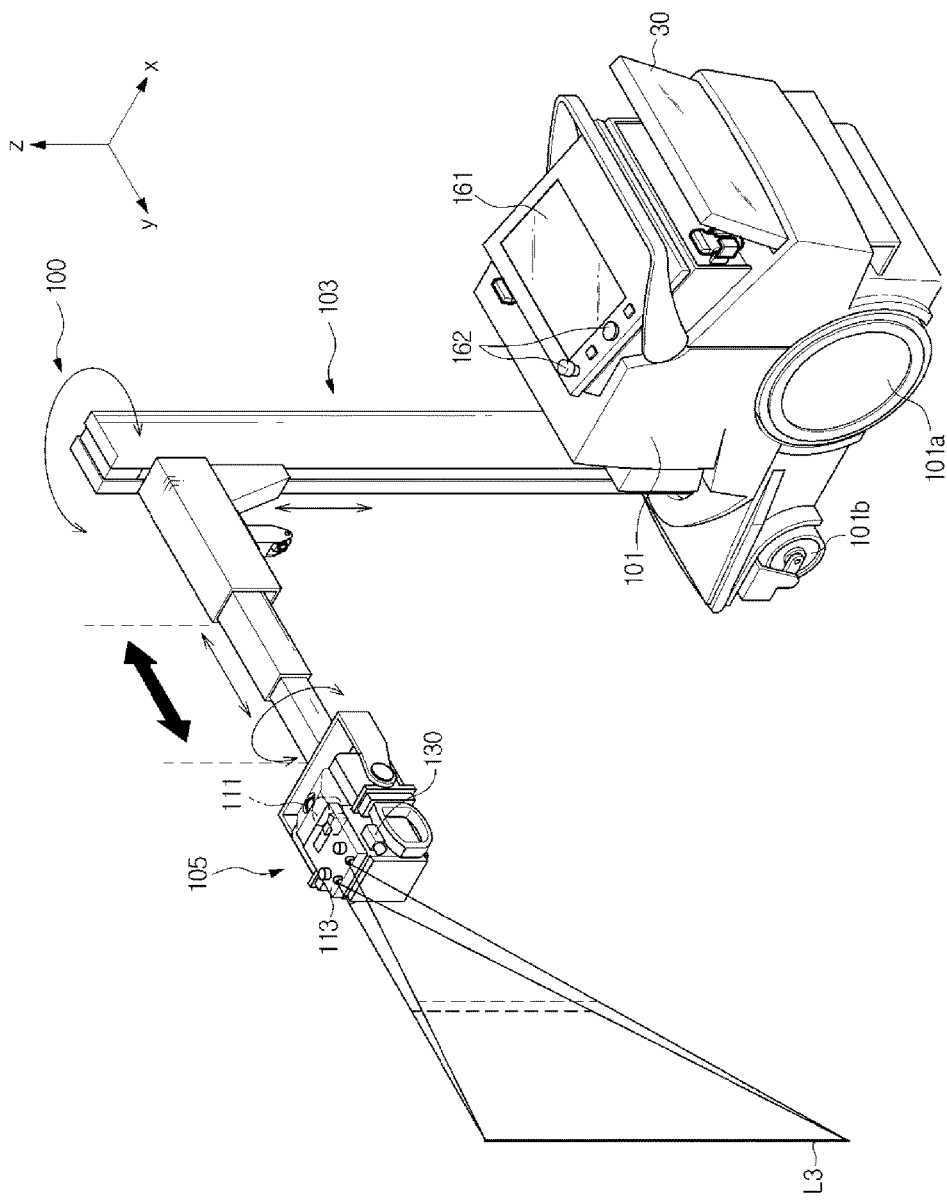
FIG. 20 is a schematic view of a position in which a light irradiated from a reference light emitter and a light irradiated from an auxiliary light emitter are overlapped when an X-ray source is rotated, in accordance with another embodiment of the present disclosure.

FIG. 19 illustrates a schematic view of imaging an object by rotating an X-ray source in accordance with another embodiment of the present disclosure, and FIG. 20 illustrates a schematic view of a position in which a light irradiated from a reference light emitter and a light irradiated from an auxiliary light emitter are overlapped when an X-ray source is rotated, in accordance with another embodiment of the present disclosure.

FIG. 2A illustrates that an X-ray imaging is performed when an object lies on the patient table 700, but when an object stands, an X-ray imaging may be performed, as illustrated in FIG. 19. That is, as illustrated in FIG. 2B, the X-ray source 105 may be rotated to allow the imaging unit 130 to face the standing object, and the reference light emitter 1000 and the at least one auxiliary light emitter 1005 may irradiate a light to a direction in which the object is placed.

For convenience of description, FIG. 20 illustrates that a light irradiated from the reference light emitter 1000 and a light irradiated from the second auxiliary light emitter 1020 are overlapped.

As illustrated in FIG. 20, when the reference light emitter 1000 and the second auxiliary light emitter 1020 face to the Y axis direction in which an object is placed since the X-ray source 105 is rotated, the reference light emitter 1000 and the second auxiliary light emitter 1020 may irradiate a light to the direction in which the object is placed. The object may stand on the Y axis, as illustrated, and the reference light emitter 1000 and the second auxiliary light emitter 1020 may irradiate a flat light diffusing a light having a fan shape in a perpendicular direction to the direction in which the object is placed. In addition, as illustrated in FIGS. 9 and 10, the reference light emitter 1000 and the second auxiliary light emitter 1020 may irradiate a light having a quadrangular pyramid shape or a conical shape.

Since the second auxiliary light emitter 1020 is provided to have a predetermined angle with respect to the reference light emitter 1000, a flat light irradiated from the reference light emitter 1000 and a flat light irradiated from the second auxiliary light emitter 1020 may be overlapped in a predetermined distance.

A user may maintain a predetermined distance between the X-ray source 105 and the X-ray detector 30 by moving the X-ray source 105 to the Y axis direction. In this case, the predetermined distance may include a case in which SID is 100 cm, 130 cm and 180 cm.

When the X-ray source 105 is apart from the X-ray detector 30 by a predetermined distance, a light irradiated from the reference light emitter 1000 and a light irradiated from the second auxiliary light emitter 1020 may be overlapped in the position of the X-ray detector 30 to be displayed as an overlapped line (L3). That is, since a distance from the reference light emitter 1000 to the overlapped line (L3), in which lights are overlapped, corresponds to a predetermined distance between the X-ray source 105 and the X-ray detector 30, a user may confirm whether the X-ray source 105 is placed in an input distance or not, via the input unit 162.

Figure 21:
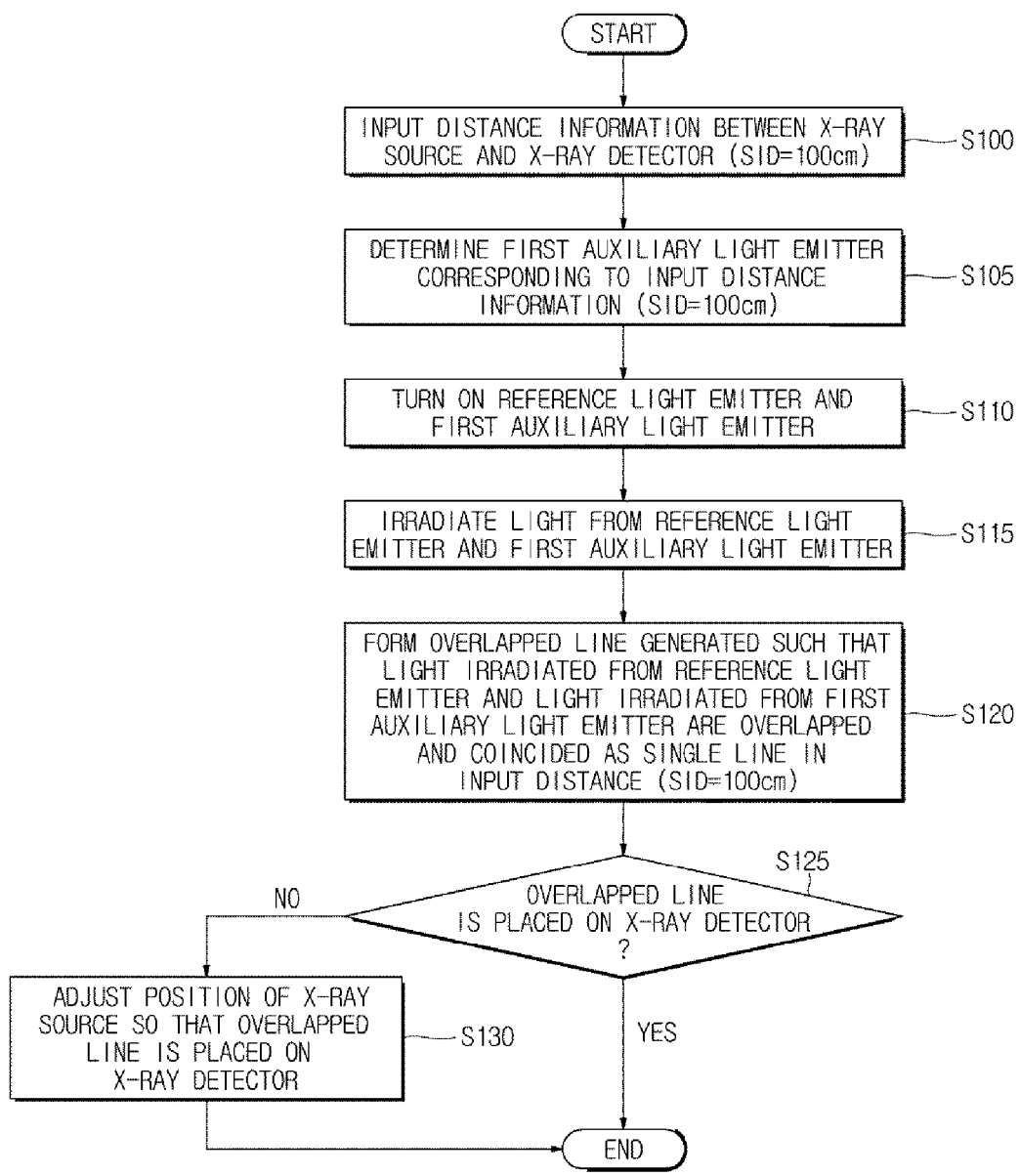
FIGS. 21 to 23 illustrate flowcharts of a control method of an X-ray imaging apparatus in accordance with an embodiment of the present disclosure.
Figure 22:
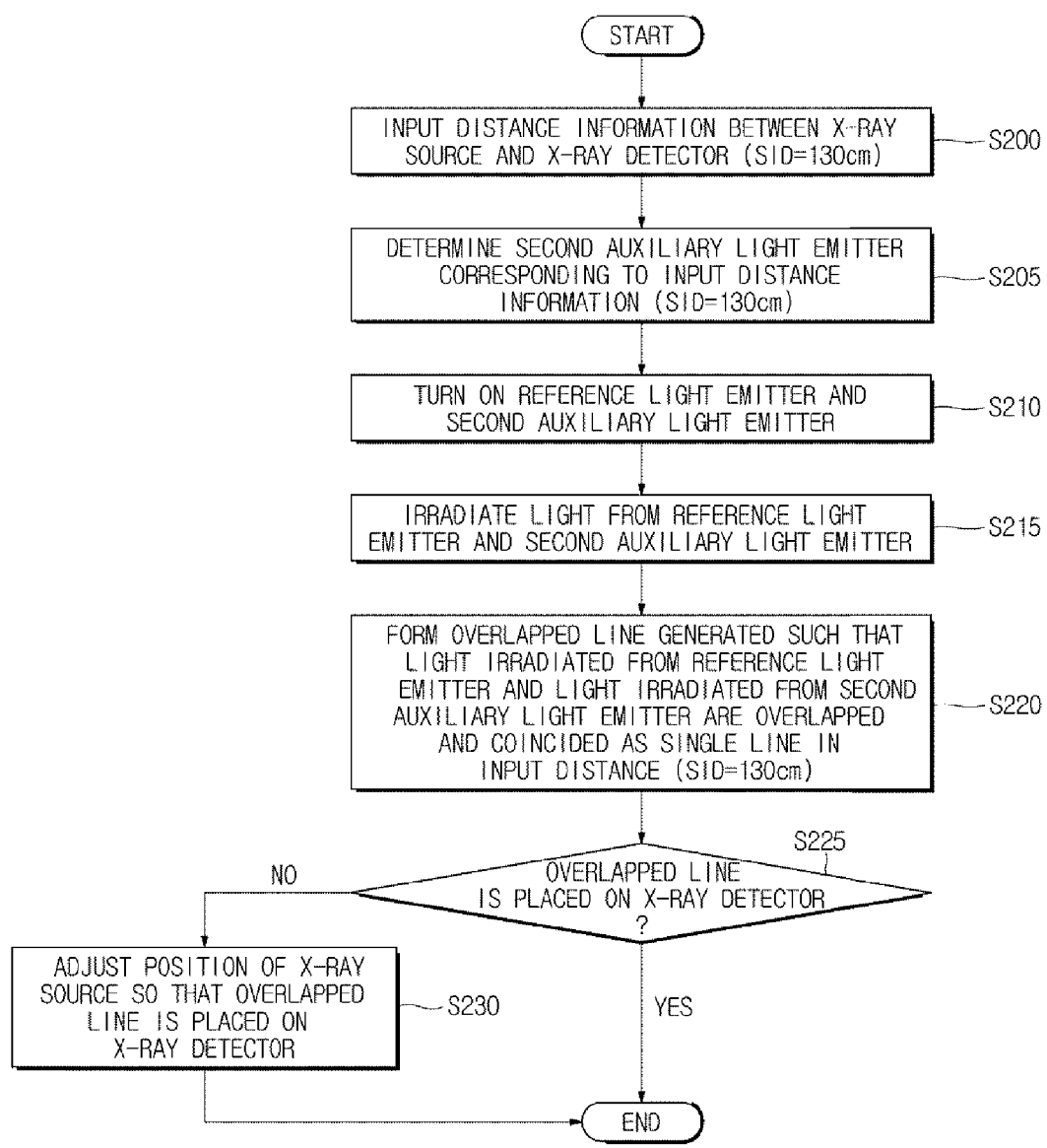
Figure 23:
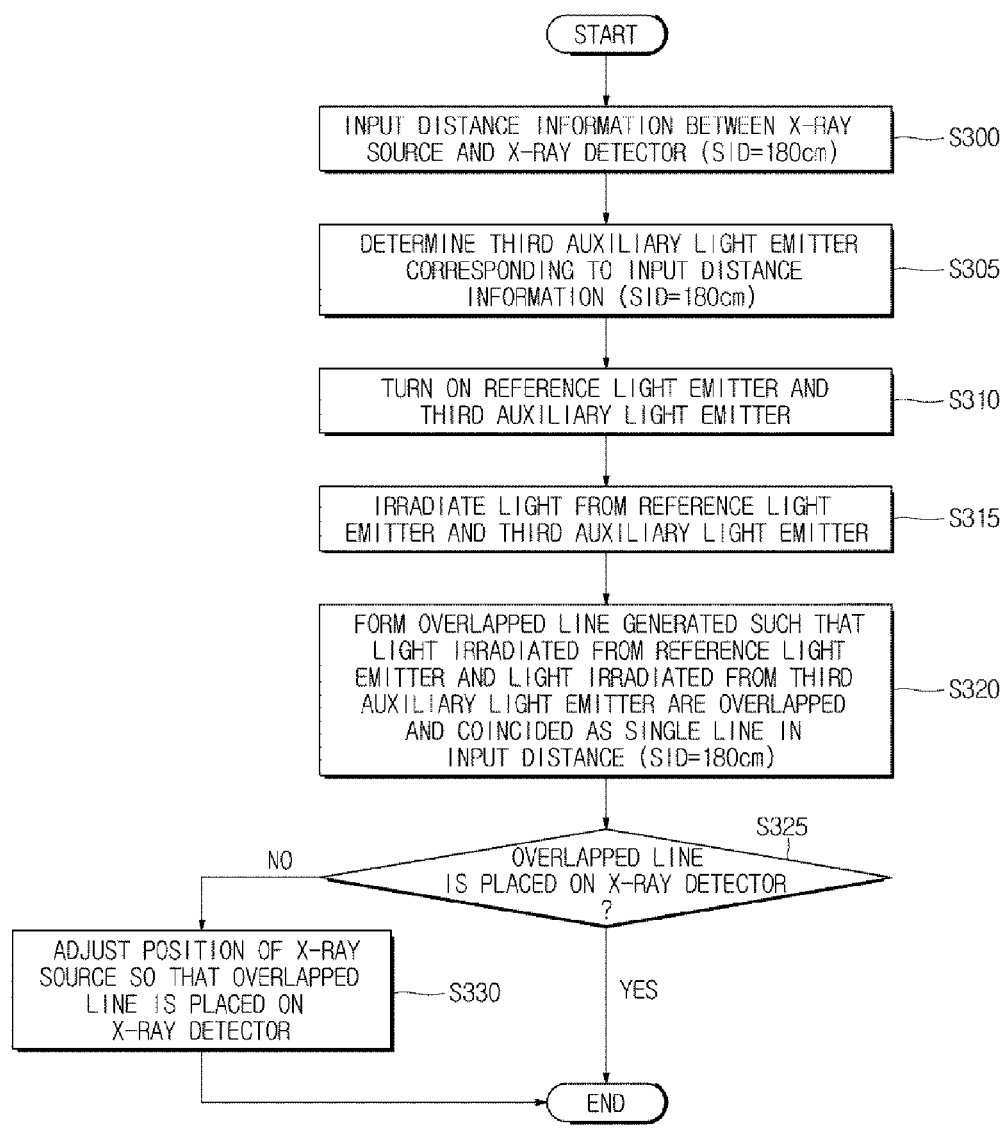

FIGS. 21 to 23 illustrate flowcharts of a control method of an X-ray imaging apparatus in accordance with an embodiment of the present disclosure.

Referring to FIG. 21, a user may input distance information between the X-ray source 105 and the X-ray detector 30 via the input unit 162 (S 100). As mentioned above, a distance between the X-ray source 105 and the X-ray detector 30 may be represented by SID, and a user may input information including that SID is 100 cm corresponding to that a distance between the X-ray source 105 and the X-ray detector 30 is 100 cm.

Based on distance information stored in the storage 170, the controller 150 may determine the first auxiliary light emitter 1010 corresponding to distance information (SID=100 cm) (S 105). In addition, the controller 150 may turn on the reference light emitter 1000 and the first auxiliary light emitter 1010 (S 110), and the controller 150 may control the reference light emitter 1000 and the first auxiliary light emitter 1010 so that a light is irradiated from the reference light emitter 1000 and the first auxiliary light emitter 1010, respectively (S115).

The lights irradiated from the reference light emitter 1000 and the first auxiliary light emitter 1010 may be overlapped and coincided in a distance (SID=100 cm) that is input from a user to form an overlapped line (L1) (S 120).

A user may determine whether the X-ray source 105 and the X-ray detector 30 becomes 100 cm since the overlapped line (L1) is placed on the X-ray detector 30 (S 125).

When it is determined that the overlapped line (L1) is not placed on the X-ray detector 30 since the distance between the X-ray source 105 and the X-ray detector 30 is shorter or longer than 100 cm, a user may manually adjust the position of the X-ray source 105 so that an X-ray imaging is performed in a state in which the distance between the X-ray source 105 and the X-ray detector 30 becomes 100 cm because the overlapped line (L1) is placed on the X-ray detector 30 (S 130).

Referring to FIG. 22, a user may input distance information (SID=130 cm) corresponding to that a distance between the X-ray source 105 and the X-ray detector 30 is 130 cm, via the input unit 162 (S 200).

Based on distance information stored in the storage 170, the controller 150 may determine the second auxiliary light emitter 1020 corresponding to distance information (SID=130 cm) (S 205). In addition, the controller 150 may turn on the reference light emitter 1000 and the second auxiliary light emitter 1020 (S 210), and the controller 150 may control the reference light emitter 1000 and the second auxiliary light emitter 1020 so that a light is irradiated from the reference light emitter 1000 and the second auxiliary light emitter 1020, respectively (S215).

The lights irradiated from the reference light emitter 1000 and the second auxiliary light emitter 1020 may be overlapped and coincided in a distance (SID=130 cm) that is input from a user to form an overlapped line (L1) (S 220).

A user may determine whether the X-ray source 105 and the X-ray detector 30 becomes 130 cm since the overlapped line (L1) is placed on the X-ray detector 30 (S 225).

When it is determined that the overlapped line (L1) is not placed on the X-ray detector 30 since the distance between the X-ray source 105 and the X-ray detector 30 is shorter or longer than 130 cm, a user may manually adjust the position of the X-ray source 105 so that an X-ray imaging is performed in a state in which the distance between the X-ray source 105 and the X-ray detector 30 becomes 130 cm because the overlapped line (L1) is placed on the X-ray detector 30 (S 230).

Referring to FIG. 23, a user may input distance information (SID=180 cm) corresponding to that a distance between the X-ray source 105 and the X-ray detector 30 is 180 cm, via the input unit 162 (S 300).

Based on distance information stored in the storage 170, the controller 150 may determine the third auxiliary light emitter 1030 corresponding to distance information (SID=180 cm) (S 305). In addition, the controller 150 may turn on the reference light emitter 1000 and the third auxiliary light emitter 1030 (S 310), and the controller 150 may control the reference light emitter 1000 and the third auxiliary light emitter 1030 so that a light is irradiated from the reference light emitter 1000 and the third auxiliary light emitter 1030, respectively (S315).

The lights irradiated from the reference light emitter 1000 and the third auxiliary light emitter 1030 may be overlapped and coincided in a distance (SID=180 cm) that is input from a user to form an overlapped line (L1) (S 320).

A user may determine whether the X-ray source 105 and the X-ray detector 30 becomes 180 cm since the overlapped line (L1) is placed on the X-ray detector 30 (S 325).

When it is determined that the overlapped line (L1) is not placed on the X-ray detector 30 since the distance between the X-ray source 105 and the X-ray detector 30 is shorter or longer than 180 cm, a user may manually adjust the position of the X-ray source 105 so that an X-ray imaging is performed in a state in which the distance between the X-ray source 105 and the X-ray detector 30 becomes 180 cm because the overlapped line (L1) is placed on the X-ray detector 30 (S 330).

Figure 24:
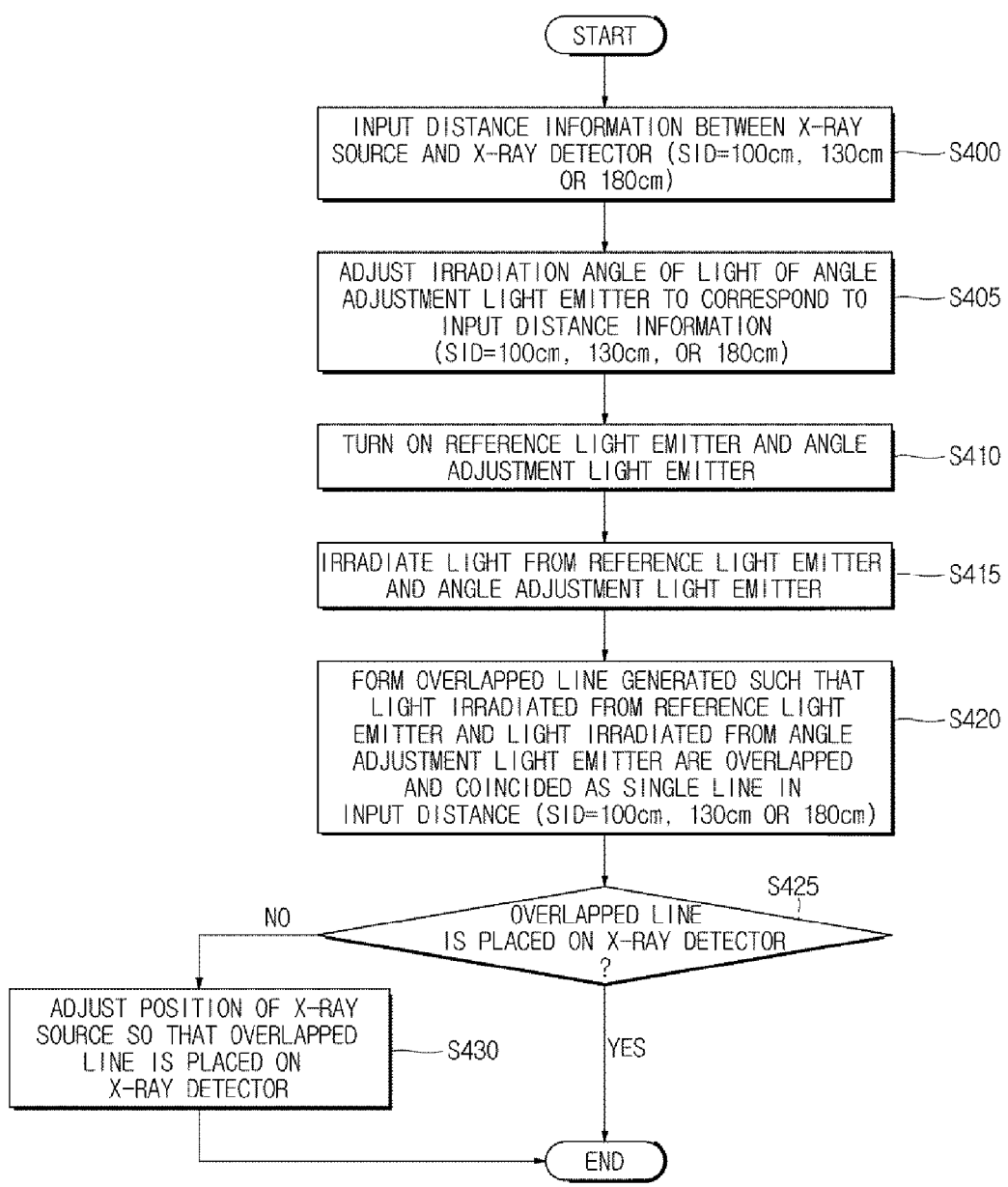
FIG. 24 illustrates a flowchart of a control method of an X-ray imaging apparatus in accordance with another embodiment of the present disclosure.

FIG. 24 illustrates a flowchart of a control method of an X-ray imaging apparatus in accordance with another embodiment of the present disclosure.

Referring to FIG. 24, a user may input distance information between the X-ray source 105 and the X-ray detector 30 via the input unit 162 (S 400). The distance information between the X-ray source 105 and the X-ray detector 30 may correspond to that SID is 100 cm, 130 cm or 180 cm.

Based on distance information stored in the storage 170 and an irradiation angle of a light of the angle adjustment light emitter 1040 corresponding to the distance information, the controller 150 may control the first driving motor 1041 and thus an irradiation angle of a light of the angle adjustment light emitter 1040 may be adjusted (S 405).

In addition, the controller 150 may turn on the reference light emitter 1000 and the angle adjustment light emitter 1040 (S 410), and the controller 150 may control the reference light emitter 1000 and the angle adjustment light emitter 1040 so that a light is irradiated from the reference light emitter 1000 and the angle adjustment light emitter 1040, respectively (S 415)

The lights irradiated from the reference light emitter 1000 and the angle adjustment light emitter 1040 may be overlapped and coincided in a distance (SID=100 cm, 130 cm or 180 cm) that is input from a user to form an overlapped line (L1) (S 420).

A user may determine whether the X-ray source 105 and the X-ray detector 30 becomes the distance that is input from a user since the overlapped line (L1) is placed on the X-ray detector 30 (S 425).

When it is determined that the overlapped line (L1) is not placed on the X-ray detector 30 since the distance between the X-ray source 105 and the X-ray detector 30 is shorter or longer than the distance that is input from a user, the user may manually adjust the position of the X-ray source 105 so that an X-ray imaging is performed in a state in which the distance between the X-ray source 105 and the X-ray detector 30 becomes the distance that is input from a user because the overlapped line (L1) is placed on the X-ray detector 30 (S 430).

Figure 25:
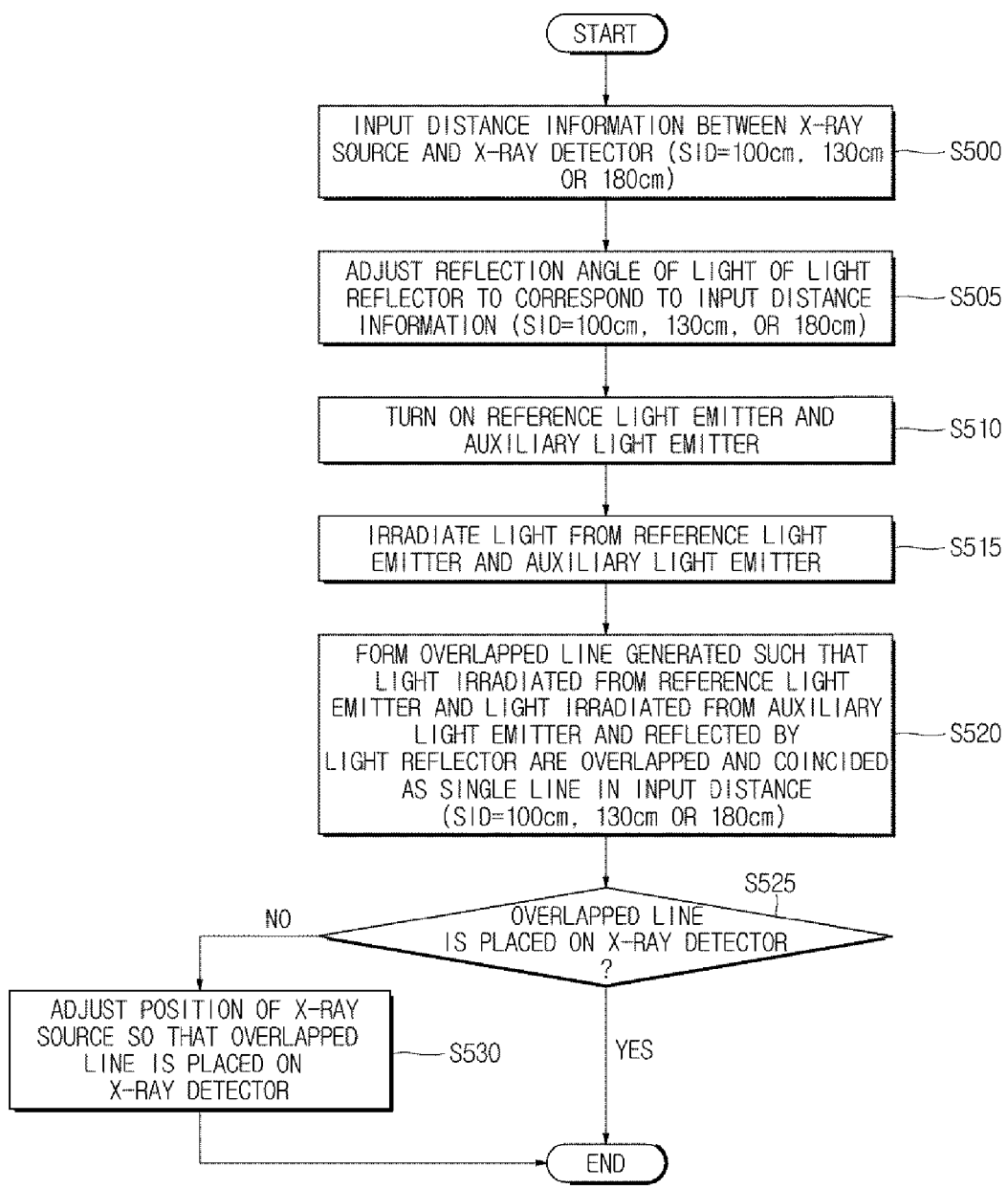
FIG. 25 illustrates a flowchart of a control method of an X-ray imaging apparatus in accordance with another embodiment of the present disclosure.

FIG. 25 illustrates a flowchart of a control method of an X-ray imaging apparatus in accordance with another embodiment of the present disclosure.

Referring to FIG. 25, a user may input distance information between the X-ray source 105 and the X-ray detector 30 via the input unit 162 (S 500). The distance information between the X-ray source 105 and the X-ray detector 30 may correspond to that SID is 100 cm, 130 cm or 180 cm.

Based on distance information stored in the storage 170 and a reflection angle of a light of the light reflector 1050 corresponding to the distance information, the controller 150 may control the second driving motor 1052 and thus the reflection angle of a light of the light reflector 1050 may be adjusted (S 505).

In addition, the controller 150 may turn on the reference light emitter 1000 and the auxiliary light emitter 1005 (S 510), and the controller 150 may control the reference light emitter 1000 and the auxiliary light emitter 1005 so that a light is irradiated from the reference light emitter 1000 and the auxiliary light emitter 1005, respectively (S 515). In this case, the auxiliary light emitter 1005 may correspond to any one of the first auxiliary light emitter 1010, the second auxiliary light emitter 1020, and the third auxiliary light emitter 1030, as mentioned above.

The light irradiated from the reference light emitter 1000 and the light, which is irradiated from the auxiliary light emitter 1005 and then reflected by the light reflector 1050, may be overlapped and coincided in a position, where is apart a distance (SID=100 cm, 130 cm or 180 cm) that is input from a user, to form an overlapped line (L1) (S 520).

A user may determine whether a distance between the X-ray source 105 and the X-ray detector 30 becomes the distance that is input from a user since the overlapped line (L1) is placed on the X-ray detector 30 (S 525).

When it is determined that the overlapped line (L1) is not placed on the X-ray detector 30 since the distance between the X-ray source 105 and the X-ray detector 30 is shorter or longer than the distance that is input from a user, the user may manually adjust the position of the X-ray source 105 so that an X-ray imaging is performed in a state in which the distance between the X-ray source 105 and the X-ray detector 30 becomes the distance that is input from a user because the overlapped line (L1) is placed on the X-ray detector 30 (S 530).

As is apparent from the above description, according to the proposed X-ray imaging apparatus and the control method thereof, it may be possible for a user to intuitively recognize whether the mobile X-ray imaging apparatus is placed in a predetermined distance with an object of X-ray imaging, based on predetermined SID information and an irradiation of light from a light emitter, and in addition, the user may easily adjust the distance between the mobile X-ray imaging apparatus and the object in a manual manner.

Although the present disclosure has been described with an exemplary embodiment, various changes and modifications may be suggested to one skilled in the art. It is intended that the present disclosure encompass such changes and modifications as fall within the scope of the appended claims.

What is claimed is:

1. An X-ray imaging apparatus comprising:
an X-ray source configured to irradiate X-rays toward an X-ray detector;
an interface configured to receive distance information between the X-ray source and the X-ray detector;
a reference light emitter configured to irradiate a light in a direction from the X-ray source to a position in which the X-ray detector is to be placed;
at least one auxiliary light emitter provided apart from the reference light emitter by a first distance and configured to irradiate a light; and
a controller configured to:
select an auxiliary light emitter among the at least one auxiliary light emitter to irradiate a light based on the distance information between the X-ray source and the X-ray detector; and
control the reference light emitter and the selected auxiliary light emitter to irradiate a light respectively so that the light from the reference light emitter and the light from the selected auxiliary light emitter overlap each other in a second distance.

2. The X-ray imaging apparatus of claim 1, wherein the at least one auxiliary light emitter is configured such that a light irradiated from the reference light emitter and a light irradiated from the at least one auxiliary light emitter have a predetermined angle.

3. The X-ray imaging apparatus of claim 1, wherein when the interface receives the distance information, the controller is further configured to turn on the reference light emitter and the selected auxiliary light emitter corresponding to the distance information so that the reference light emitter irradiates a light and the auxiliary light emitter irradiates a light.

4. The X-ray imaging apparatus of claim 1, wherein a light irradiated from the reference light emitter and a light irradiated from the selected auxiliary light emitter are overlapped and coincided as a single line to form an overlapped line in the second distance.

5. The X-ray imaging apparatus of claim 4, wherein the X-ray source is configured to be movable so that the overlapped line is placed on the X-ray detector.

6. The X-ray imaging apparatus of claim 1, wherein the reference light emitter and the selected auxiliary light emitter are disposed adjacent to the X-ray source to face the X-ray detector.

7. The X-ray imaging apparatus of claim 1, wherein the reference light emitter and the at least one auxiliary light emitter comprise a Light Emitting Diode (LED) or Light Amplification by Simulated Emission of Radiation (LASER) diode.

8. The X-ray imaging apparatus of claim 1, further comprising:
a storage configured to store the distance information between the X-ray source and the X-ray detector.

9. The X-ray imaging apparatus of claim 8, wherein the storage is further configured to store a corresponding relation between the stored distance information and the at least one auxiliary light emitter.

10. An X-ray imaging apparatus comprising:
an X-ray source configured to irradiate X-rays toward an X-ray detector;
an interface configured to receive distance information between the X-ray source and the X-ray detector;
a reference light emitter configured to irradiate a light in a direction from the X-ray source to a position in which the X-ray detector is to be placed;
an angle adjustment light emitter configured to adjust an irradiation angle of a light based on the distance information to irradiate a light; and
a controller configured to:
adjust an irradiation angle of a light of the angle adjustment light emitter based on the distance information; and
control the reference light emitter and the angle adjustment light emitter to irradiate a light respectively so that the light from the reference light emitter and the light from the angle adjustment light emitter are configured to overlap each other.

11. The X-ray imaging apparatus of claim 10, wherein the angle adjustment light emitter comprises a first driving motor configured to rotate the angle adjustment light emitter.

12. The X-ray imaging apparatus of claim 10, wherein when the interface receives the distance information, the controller is further configured to adjust an irradiation angle of a light of the angle adjustment light emitter so that a light capable of being overlapped with a light irradiated from the reference light emitter in an input distance is irradiated.

13. The X-ray imaging apparatus of claim 10, wherein a light irradiated from the reference light emitter and a light irradiated from the angle adjustment light emitter are overlapped and coincided as a single line to form an overlapped line in a predetermined distance.

14. An X-ray imaging apparatus comprising:
an X-ray source configured to irradiate X-rays toward an X-ray detector;
an interface configured to receive distance information between the X-ray source and the X-ray detector;
a reference light emitter configured to irradiate a light in a direction from the X-ray source to a position in which the X-ray detector is to be placed;
at least one auxiliary light emitter configured to irradiate a light;
a light reflector provided apart from the at least one auxiliary light emitter by a first distance and configured to reflect a light irradiated from the at least one auxiliary light emitter; and
a controller configured to:
adjust a reflection angle of a light of the light reflector based on the distance information; and
control the reference light emitter and the at least one auxiliary light emitter to irradiate a light respectively so that the light from the reference light emitter and the light from the at least one auxiliary light emitter are configured to overlap each other in a second distance.

15. The X-ray imaging apparatus of claim 14, wherein the light reflector is further configured to adjust a reflection angle of a light based on the distance information so that a light irradiated from the reference light emitter and the reflected light are overlapped.

16. The X-ray imaging apparatus of claim 14, wherein the light reflector comprises a second driving motor configured to rotate the light reflector.

17. The X-ray imaging apparatus of claim 14, wherein the reference light emitter and the auxiliary light emitter are disposed adjacent to the X-ray source to face the X-ray detector.

* * * * *